US006933105B2

(12) United States Patent  
Jin

(10) Patent No.: US 6,933,105 B2  
(45) Date of Patent: Aug. 23, 2005

(54) RESISTANCE SEQUENCES AND USES THEREOF

(75) Inventor: Shengfang Jin, West Roxbury, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 514 days.

(21) Appl. No.: 09/774,490

(22) Filed: Jan. 31, 2001

(65) Prior Publication Data

US 2001/0034332 A1 Oct. 25, 2001

Related U.S. Application Data

(60) Provisional application No. 60/179,191, filed on Jan. 31, 2000.

(51) Int. Cl.[7] .......................... C12Q 1/68; G01N 33/53
(52) U.S. Cl. ............................. 435/4; 435/6; 435/7.1; 436/501; 436/503; 436/504
(58) Field of Search .................... 435/4, 6, 7.1, 503, 435/504; 436/501

(56) References Cited

U.S. PATENT DOCUMENTS

| | | | |
|---|---|---|---|
| 5,585,277 A | 12/1996 | Bowie et al. | 436/518 |
| 5,679,582 A | 10/1997 | Bowie et al. | 436/518 |
| 5,736,326 A | 4/1998 | Scanlon | 435/6 |
| 5,905,023 A | 5/1999 | Sager et al. | 435/6 |
| 5,932,422 A | * 8/1999 | Shyjan | |

FOREIGN PATENT DOCUMENTS

WO    WO 96/27611    9/1996

OTHER PUBLICATIONS

Barrand et al, British Journal of Cancer, 1992, vol. 65, pp. 239–245.*
Stein et al, Proc Annu Meet Am Assoc Cancer Res, 1997, vol. 38, p. A3215.*
Nilsen–Hamilton et al, Gene, 1987, vol. 51, pp. 163–170.*
Rieger et al, Glossary of Genetics, 1991, p. 190, p. 479 and p. 480.*
Teicher et al, Science, 1990, vol. 247, pp. 1457–1461.*
Verma et al (Nature, 1997, vol. 389, pp. 239–242).*
Eck et al (Gene–Based Therapy, In: The Pharmacological Basis of Therapeutics, Goodman and Gilman, Ed.s, 1996, pp. 77–10.*
Orkin et al ("Report and Recommendation of the Panel to Assess the NIH Investment in Research on Gene Therapy", NIH, 1995).*
Accession No. X81627, Garay–Rojas et al., Oct. 3, 1997.
Accession No. W13166, Marra et al., Oct. 2, 1997.
Accession No. K03235, Linzer et al., Apr. 27, 1993.
Accession No. X85993, Puschel et al., Jul. 8, 1996.
Accession No. L26081, Kolodkin et al., May 8, 1995.
Accession No. M25280, Siegelman et al., Oct. 7, 1998.
Accession No. M25324, Lasky et al., Apr. 27, 1993.
Accession No. M92357, Sarma et al., Jun. 7, 1993.
Accession No. L24118, Wolf et al., Jul. 14, 1994.
Accession No. U04313, Zhou et al., Jun. 11, 1994.
Accession No. U54705, Zhang et al., Aug. 15, 1996.
Yamada et al., "Identification of semaphorin E as a non–MDR drug resistance gene of human cancers" Proc. Nat'l. Acad. Sci. USA 94:14713–14718, Dec. 1997.

* cited by examiner

*Primary Examiner*—Karen A. Canella
(74) *Attorney, Agent, or Firm*—Fish & Richardson P.C.

(57) ABSTRACT

Increased expression of resistance sequences is associated with drug resistance of certain cells (e.g., cancer cells). The invention provides methods for identifying drug resistant cells by measuring the expression or activity of resistance genes (e.g., semaphorin D, B94, mel-14 antigen, 24p3, proliferin, or maspin), methods for identifying modulators of drug resistance, and methods for modulating drug resistance by modulating the expression or activity of resistance sequences.

33 Claims, 7 Drawing Sheets

```
AATCTTTTATTTTATCGATGTTAACAAGCTTAGTAATCGATGCCACGTCGAGGGGTGTCGACC
CACGCGTCCGGGAGTAGGTTGAGCTCGCCTGTTCTCCCATTGTCAGCCAGTCTATTTCCAG
ATTGTTTGAACTTCTCTGGCCGCACAATACAGGAAGGAAGACTAAAGCAGCAAAGGGACCTA
CAGCGTCTGCAGCATGGGCTGGTTAACTAGGATTGTCTGTCTTTTCTGGGGAGTATTACTTA
CAGCAAGAGCAAACTATCAGAATGGGAAGAACAATGTGCCAAGGCTGAAATTATCCTACAAA
GAAATGTTGGAATCCAACAATGTGATCACTTTCAATGGCTTGGCCAACAGCTCCAGTTATCAT
ACCTTCCTTTTGGATGAGGAACGGAGTAGGCTGTATGTTGGAGCAAAGGATCACATATTTTC
ATTCGACCTGGTTAATATCAAGGATTTTCAAAAGATTGTGTGGCCAGTATCTTACACCAGAAG
AGATGAATGCAAGTGGGCTGGAAAAGACATCCTGAAAGAATGTGCTAATTTCATCAAGGTAC
TTAAGGCATATAATCAGACTCACTTGTACGCCTGTGGAACGGGGGCTTTTCATCCAATTTGC
ACCTACATTGAAATTGGACATCATCCTGAGGACAATATTTTTAAGCTGGAGAACTCACATTTT
GAAAACGGCCGTGGGAAGAGTCCATATGACCCTAAGCTGCTGACAGCATCCCTTTTAATAGA
TGGAGAATTATACTCTGGAACTGCAGCTGATTTTATGGGGCGAGACTTTGCTATCTTCCGAA
CTCTTGGGCACCACCACCCAATCAGGACAGAGCAGCATGATTCCAGGTGGCTCAATGATCC
AAAGTTCATTAGTGCCCACCTCATCTCAGAGAGTGACAATCCTGAAGATGACAAAGTATACTT
TTTCTTCCGTGAAAATGCAATAGATGGAGAACACTCTGGAAAAGCTACTCACGCTAGAATAG
GTCAGATATGCAAGAATGACTTTGGAGGGCACAGAAGTCTGGTGAATAAATGGACAACATTC
CTCAAAGCTCGTCTGATTTGCTCAGTGCCAGGTCCAAATGGCATTGACACTCATTTTGATGA
ACTGCAGGATGTATTCCTAATGAACTTTAAAGATCCTAAAAATCCAGTTGTATATGGAGTGTT
TACGACTTCCAGTAACATTTTCAAGGGATCAGCCGTGTGTATGTATAGCATGAGTGATGTGA
GAAGGGTGTTCCTTGGTCCATATGCCCACAGGGATGGACCCAACTATCAATGGGTGCCTTAT
CAAGGAAGAGTCCCCTATCCACGGCCAGGAACTTGTCCCAGCAAAACATTTGGTGGTTTTGA
CTCTACAAAGGACCTTCCTGATGATGTTATAACCTTTGCAAGAAGTCATCCAGCCATGTACAA
TCCAGTGTTTCCTATGAACAATCGCCCAATAGTGATCAAAACGGATGTAAATTATCAATTTAC
ACAAATTGTCGTAGACCGAGTGGATGCAGAAGATGGACAGTATGATGTTATGTTTATCGGAA
CAGATGTTGGGACCGTTCTTAAAGTAGTTTCAATTCCTAAGGAGACTTGGTATGATTTAGAAG
AGGTTCTGCTGGAAGAAATGACAGTTTTTCGGGAACCGACTGCTATTTCAGCAATGGAGCTT
TCCACTAAGCAGCAACAACTATATATTGGTTCAACGGCTGGGGTTGCCCAGCTCCCTTTACA
CCGGTGTGATATTTACGGGAAAGCGTGTGCTGAGTGTTGCCTCGCCCGAGACCCTTACTGT
GCTTGGGATGGTTCTGCATGTTCTCGCTATTTTCCCACTGCAAAGAGACGCACAAGACGACA
AGATATAAGAAATGGAGACCCACTGACTCACTGTTCAGACTTACACCATGATAATCACCATG
GCCACAGCCCTGAAGAGAGAATCATCTATGGTGTAGAGAATAGTAGCACATTTTTGGAATGC
AGTCCGAAGTCGCAGAGAGCGCTGGTCTATTGGCAATTCCAGAGGCGAAATGAAGAGCGAA
AAGAAGAGATCAGAGTGGATGATCATATCATCAGGACAGATCAAGGCCTTCTGCTACGTAGT
```

FIG. 1A

CTACAACAGAAGGATTCAGGCAATTACCTCTGCCATGCGGTGGAACATGGGTTCATACAAAC
TCTTCTTAAGGTAACCCTGGAAGTCATTGACACAGAGCATTTGGAAGAACTTCTTCATAAAGA
TGATGATGGAGATGGCTCTAAGACCAAAGAAATGTCCAATAGCATGACACCTAGCCAGAAGG
TCTGGTACAGAGACTTCATGCAGCTCATCAACCACCCCAATCTCAACACGATGGATGAGTTC
TGTGAACAAGTTTGGAAAAGGGACCGAAAACAACGTCGGCAAAGGCCAGGACATACCCCAG
GGAACAGTAACAAATGGAAGCACTTACAAGAAAATAAGAAAGGTAGAAACAGGAGGACCCA
CGAATTTGAGAGGGCACCCAGGAGTGTCTGAGCTGCATTACCTCTAGAAACCTCAAACAAGT
AGAAACTTGCCTAGACAATAACTGGAAAAACAAATGCAATATACATGAACTTTTTTCATGGCA
TTATGTGGATGTTTACAATGGTGGGAAATTCAGCTGAGTTCCACCAATTATAAATTAAATCCA
TGAGTAACTTTCCTAATAGGCTTTTTTTTCCTAATACC (SEQ ID NO:1)

FIG. 1B

GACAACAGGTAGAAAAATTCCTGGGCTCAGGCTGGAGTGACACCCTTTTCTTTCCCTAACAT
CTTCTACTCAGATACCTAAATTTAAGATTCAGGACAGCTGTCCCCAACTCTTACCATGTCTTT

TATAACTTGCTCCTTAACTTGCCCAACCTGTAGGCTATCTCATTTTCTCGCTTCACTCTGCAA
GGTTTATAACATGATGAATTTAAATAC (SEQ ID NO:2)   FIG. 2B

```
GAATTCTCGAGCTCGTCGACCACGCCCTCCTTGTGCAAGAACTCTGAGCCCCAGGTGCAGG
AGGCTGAGGCCTGCAGAGAGACTTGCAGAGAGACCCAGCAAGCCATGGTGTTTCCATGGA
GATGTGAGGGTACTTACTGGGGCTCGAGGAACATCCTGAAGCTGTGGGTCTGGACACTGCT
CTGTTGTGACTTCCTGATACACCATGGAACTCACTGTTGGACTTACCATTATTCTGAAAAGCC
CATGAACTGGGAAAATGCTAGAAAGTTCTGCAAGCAAAATTACACAGATTTAGTCGCCATAC
AAAACAAGAGAGAAATTGAGTATTTAGAGAATACATTGCCCAAAAGCCCTTATTACTACTGGA
TAGGAATCAGGAAAATTGGGAAAATGTGGACATGGGTGGGAACCAACAAAACTCTCACTAAA
GAAGCAGAGAACTGGGGTGCTGGGGAGCCCAACAACAAGAAGTCCAAGGAGGACTGTGTG
GAGATCTATATCAAGAGGGAACGAGACTCTGGGAAATGGAACGATGACGCCTGTCACAAAC
GAAAGGCAGCTCTCTGCTACACAGCCTCTTGCCAGCCAGGGTCTTGCAATGGCCGTGGAGA
ATGTGTGGAAACTATCAACAATCACACGTGCATCTGTGATGCAGGGTATTACGGGCCCCAGT
GTCAGTATGTGGTCCAGTGTGAGCCTTTGGAGGCCCCTGAGTTGGGTACCATGGACTGCAT
CCACCCCTTGGGAAACTTCAGCTTCCAGTCCAAGTGTGCTTTCAACTGTTCTGAGGGAAGAG
AGCTACTTGGGACTGCAGAAACACAGTGTGGAGCATCTGGAAACTGGTCATCTCCAGAGCC
AATCTGCCAAGTGGTCCAGTGTGAGCCTTTGGAGGCCCCTGAGTTGGGTACCATGGACTGC
ATCCACCCCTTGGGAAACTTCAGCTTCCAGTCCAAGTGTGCTTTCAACTGTTCTGAGGGAAG
AGAGCTACTTGGGACTGCAGAAACACAGTGTGGAGCATCTGGAAACTGGTCATCTCCAGAG
CCAATCTGCCAAGAGACAAACAGAAGTTTCTCAAAGATCAAAGAAGGTGACTACAACCCCCT
CTTCATTCCTGTAGCCGTCATGGTCACCGCATTCTCGGGGCTGGCATTTCTCATTTGGCTGG
CAAGGCGGTTAAAAAAAGGCAAGAAATCTCAAGAAAGGATGGATGATCCATACTGATTCATC
CTTTGTGAAAGGAAAGCCATGAAGTGCTAAAGACAAAACATTGGAAAATAACGTCAAGTCCT
CCCGTGAAGATTTTACACGCAGGCATCTCCCACATTAGAGATGCAGTGTTTGCTCAACGAAT
CTGGAAGGATTTCTTCATGACCAACAGCTCCTCCTAATTTCCCCTCGCTCATTCATCCCATTA
ACCCTATCCCATAATGTGTGTCTATACAGAGTAGTATTTTATCATCTTTTCTGTGGAGGAACA
AGCAAAAGTGTTACTGTAGAATATAAAGACAGCTGCTTTTACTCTTTCCTAACTCTTGTTTCCT
AGTTCAATTCAGCACAGAAGCTAATGCCAAACACAGTGAAAATATGATCCATGAGTAATTGGA
AACTCAGACTCCTTGCGCATAGTACGTACCCTATGTAACATCGACAAAAATCTTTCATTTCCA
CCTCCAAAGAACAGTGCTCTATTCAAGTTGGGAAAGTCCTACTTCCTCTGTAGACCCACTAT
CTGTGAGTGACAGCCACTGTAGCTGTTCACATTAACCTTCCCCATCTCCTTTTCCTAGGAGA
ATAATTCCACACACTGCACCCCATGATGGCCACCAAACATCAAAGAAGGGAAAATCTCCTGC
ATTGAGTTTTAGTTTTGAGTTTTCCCTTCTCTTTATTAGATCTCTGATGGTTCCTTGAAGTCAG
TGTTCTGATGATTATTAATAGTTAATGATAACACAACCCACTCTCTTGGAGCTGATGTTATGAA
```

FIG. 2A

GTCGACCCACGCGTCCGCAGACCTAGTAGCTGTGGAAACCATGGCCCTGAGTGTCATGTGT
CTGGGCCTTGCCCTGCTTGGGGTCCTGCAGAGCCAGGCCCAGGACTCAACTCAGAACTTGA
TCCCTGCCCCATCTCTGCTCACTGTCCCCCTGCAGCCAGACTTCCGGAGCGATCAGTTCCG
GGGCAGGTGGTACGTTGTGGGCCTGGCAGGCAATGCGGTCCAGAAAAAAACAGAAGGCAG
CTTTACGATGTACAGCACCATCTATGAGCTACAAGAGAACAATAGCTACAATGTCACCTCCAT
CCTGGTCAGGGACCAGGACCAGGGCTGTCGCTACTGGATCAGAACATTTGTTCCAAGCTCC
AGGGCTGGCCAGTTCACTCTGGGAAATATGCACAGGTATCCTCAGGTACAGAGCTACAATG
TGCAAGTGGCCACCACGGACTACAACCAGTTCGCCATGGTATTTTTCCGAAAGACTTCTGAA
AACAAGCAATACTTCAAAATTACCCTGTATGGAAGAACCAAGGAGCTGTCCCTGAACTGAA
GGAACGTTTCACCCGCTTTGCCAAGTCTCTGGGCCTCAAGGACGACAACATCATCTTCTCTG
TCTGTCTGCCACTCCATCTTTCCTGTTGCCAGAGAGCCACCTGGCTGCCCCACCAGCCACC
ATACCAAGGAGCATCTGGAGCCTCTTCTTATTTGGCCAGCACTCCCCATCCACCTGTCTTAA
CACCACCAATGGCGTCCCCTTTCTGCTGAATAAATACATGCCCCCAAAAAAAAAAAAAAAGG
GCGGCCGC (SEQ ID NO:3)

FIG. 3A

MALSVMCLGLALLGVLQSQAQDSTQNLIPAPSLLTVPLQPDFRSDQFRGRWYVVGLAGNAVQK
KTEGSFTMYSTIYELQENNSYNVTSILVRDQDQGCRYWIRTFVPSSRAGQFTLGNMHRYPQVQS
YNVQVATTDYNQFAMVFFRKTSENKQYFKITLYGRTKELSPELKERFTRFAKSLGLKDDNIIFSVC
LPLHLSCCQRATWLPHQPPYQGASGASSYLASTPHPPVLTPPMASPFC (SEQ ID NO:4)

FIG. 3B

CCCCTTTTGGTTTTTGTTCTATCGACCCTAACAAGCTTAGTAATCGATGCCACTCGAGGCCAA
GAATTCATTACGAGCCTGAGCTCCTTCGGCTTTTTCCCCCCTTTTGCATCTTGTTTCCCGGGA
TACCTGCAACTCAAGGATGGATGCCCTGAGACTGGCAAATTCAGCTTTTGCTGTTGACTTGT
TCAAACAACTATGTGAAAGGGACCCAGCAGGAAACATTCTCTTCTCTCCAATATGCCTCTCTA
CTTCTCTGTCCCTTGCGCAAGTGGGCACCAAAGGCGACACAGCAAATGAAATTGGACAGGT
CCTTCATTTTGAGAATGTCAAAGATGTACCCTTTGGGTTTCAAACAGTCACTTCTGATGTTAA
TAAGCTCAGTTCTTTTTACTCTTTGAAACTTGTCAAGCGACTCTACATAGACAAATCTCTGAAC
CCTTCTACAGAATTTATCAGTTCTACCAAAAGACCATATGCAAAAGAATTGGAAACTGTTGAC
TTCAAAGACAAACTGGAAGAAACGAAAGGTCAAATTAACAGCTCCATTAAGGAGCTCACAGA
TGGCCACTTTGAGGACATTTTGTCAGAGAACAGTATAAGTGACCAGACCAAAATCCTTGTGG
TTAATGCTGCCTACTTTGTTGGAAAGTGGATGAAGAAATTTCCGGAATCAGAAACAAAAGAAT
GTCCTTTCAGAATCAGCAAGACAGACACCAAACCCGTACAAATGATGAATCTTGAGGCCACT
TTCTGCTTGGGTAACATTGATGACATCAGCTGTAAGATCATAGAACTTCCTTTCCAGAATAAG
CATCTGAGTATGCTCATTGTGCTCCCCAAGGACGTGGAGGATGAGTCCACAGGCCTGGAGA
AGATTGAACAGCAACTCAACCCAGAAACATTGTTACAGTGGACCAACCCCAGTACCATGGCC
AATGCCAAAGTCAAACTTTCCCTCCCAAAGTTTAAGGTAGAAAAGATGATTGATCCCAAGGCT
AGTCTGGAAAGCCTAGGGCTGAAAAGTCTCTTCAATGAAAGTACATCGGATTTCTCTGGAAT
GTCAGAGACCAAGGGAGTGTCCCTGTCAAATGTGATTCATAGAGTATGCCTAGAAATAACCG
AAGATGGTGGTGAGTCCATCGAGGTGCCAGGGTCCCGGATCTTACAGCACAAGGATGAATT
CAATGCTGACCATCCATTTATTTATATCATTAGACACAACAAAACTCGAAACATCATTTTCTTT
GGCAAATTCTGTTCTCCTTAGCTGGCAGGGCCTTGCCAAGTCTCAGGGAACTTGTCTGTAGT
CGCAGAGCTCTGTAAACTTTGTATCCAGACAATCACTTTCTATACAATAAATTGTAAATGTTG
CTGAAAAAAAAAAAAAAAAAAAAAAAA (SEQ ID NO:5)

FIG. 4

```
GGTGGAGACTAAATATAATCTTTTATTTTATCGATGTTAACAAGCTTAGTAATCGATGCCACG
TCGAGGGGTGTCGACCCACGCGTCTCGCTTGCCTGTTCCTTTTCCACGCATTTTCCAGGATA
ACTGTGACTCCAGGCCCGCAATGGATGCCCTGCAACTAGCAAATTCGGCTTTTGCCGTTGAT
CTGTTCAAACAACTATGTGAAAAGGAGCCACTGGGCAATGTCCTCTTCTCTCCAATCTGTCT
CTCCACCTCTCTGTCACTTGCTCAAGTGGGTGCTAAAGGTGACACTGCAAATGAAATTGGAC
AGGTTCTTCATTTTGAAAATGTCAAAGATGTACCCTTTGGATTTCAAACAGTAACATCGGATG
TAAACAAACTTAGTTCCTTTTACTCACTGAAACTAATCAAGCGGCTCTACGTAGACAAATCTC
TGAATCTTTCTACAGAGTTCATCAGCTCTACGAAGAGACCCTATGCAAAGGAATTGGAAACT
GTTGACTTCAAAGATAAATTGGAAGAAACGAAAGGTCAGATCAACAACTCAATTAAGGATCTC
ACAGATGGCCACTTTGAGAACATTTTAGCTGACAACAGTGTGAACGACCAGACCAAAATCCT
TGTGGTTAATGCTGCCTACTTTGTTGGCAAGTGGATGAAGAAATTTCCTGAATCAGAAACAAA
AGAATGTCCTTTCAGAGTCAACAAGACAGACACCAAACCAGTGCAGATGATGAACATGGAGG
CCACGTTCTGTATGGGAAACATTGACAGTATCAATTGTAAGATCATAGAGCTTCCTTTTCAAA
ATAAGCATCTCAGCATGTTCATCCTACTACCCAAGGATGTGGAGGATGAGTCCACAGGCTTG
GAGAAGATTGAAAAACAACTCAACTCAGAGTCACTGTCACAGTGGACTAATCCCAGCACCAT
GGCCAATGCCAAGGTCAAACTCTCCATTCCAAAATTTAAGGTGGAAAAGATGATTGATCCCA
AGGCTTGTCTGGAAAATCTAGGGCTGAAACATATCTTCAGCGAAGACACATCTGATTTCTCT
GGAATGTCAGAGACCAAGGGAGTGGCCCTATCAAATGTTATCCACAAAGTGTGCTTAGAAAT
AACTGAAGATGGTGGGGATTCCATAGAGGTGCCAGGAGCACGGATCCTGCAGCACAAGGAT
GAATTGAATGCTGACCATCCCTTTATTTACATCATCAGGCACAACAAAACTCGAAACATCATT
TTCTTTGGCAAATTCTGTTCTCCTTAAGTGGCATAGCCCATGTTAAGTCCTCCCTGACTTTTC
TGTGGATGCCGATTTCTGTAAACTCTGCATCCAGAGATTCATTTTCTAGATACAATAAATTGC
TAATGTTGCTGGATCAGGAAGCCGCCAGTACTTGTCATATGTAGCCTTCACACAGATAGACC
TTTTTTTTTTTTCCAATTCTATCTTTTGTTTCCTTTTTTCCCATAAGACAATGACATACGCTTTT
AATGAAAAGGAATCACGTTAGAGGAAAAATATTTATTCATTATTTGTCAAATTGTCCGGGGTA
GTTGGCAGAAATACAGTCTTCCACAAAGAAAATTCCTATAAGGAAGATTTGGAAGCTCTTCTT
CCCAGCACTATGCTTTCCTTCTTTGGGATAGAGAATGTTCCAGACATTCTCGCTTCCCTGAAA
GACTGAAGAAAGTGTAGTGCATGGGACCCACGAAACTGCCCTGGCTCCAGTGAAACTTGGG
CACATGCTCAGGCTACTATAGGTCCAGAAGTCCTTATGTTAAGCCCTGGCAGGCAGGTGTTT
ATTAAAATTCTGAATTTTGGGGATTTTCAAAAGATAATATTTTACATACACTGTATGTTATAGAA
CTTCATGGATCAGATCTGGGGCAGCACCCTATAAATCACCACCTTAATATGCTGCAACAAAA
TGTAGAATATTCAGACAAAATGGATACATAAAGACTAAGTAGCCCATAAGGGGTCAAATTTTG
CTGCCAAATGCGTATGCCACCAACTTACAAAAACACTTCGTTCGCAGAGCTTTTCAGATTGT
```

FIG. 5A

```
GGAATGTTGGATAAGGAATTATAGACCTCTAGTAGCTGAAATGCAAGACCCCAAGAGGAAGT
TCAGATCTTAA (SEQ ID NO:6)
```

FIG. 5B

| | Semaphorin D | Maspin | B94 | mel-14 Antigen | 24p3 | Proliferin |
|---|---|---|---|---|---|---|
| Expression in EMT6 tumors | Up-regulated in CDDP resistant tumor | Down-regulated in CDDP resistant tumor | Up-regulated in CDDP resistant tumor | Up-regulated in CDDP resistant tumor | Up-regulated in CDDP resistant tumor | Up-regulated in CDDP resistant tumor |
| Expression in EMT6 cell lines | Remain up-regulated in CDDP resistant cell line to passage 13 (passage 3, 6, 10, and 13 checked) | Remain down-regulated in CDDP resistant cell line to passage 3 | Remain up-regulated in CDDP resistant cell line to passage 10 | Remain up-regulated in CDDP resistant cell line to passage 10 | Remain up-regulated in CDDP resistant cell line to passage 10 | Remain up-regulated in CDDP resistant cell line to passage 10 |
| Expression in multi-cell line pairs (A2780, UCLA, U937, HL60, SCC25 pairs) | Higly expressed in SCC25 CDDP cell line, not significantly expressed in other cell line pairs. | Highly expressed in SCC25 wild type cell line (and HL60 AD cell line), not significantly expressed in other cell line pairs. | Differentially expressed in HL60 and U937 cell lines (lower in resistant cell line). | Differentially expressed in HL60 cell lines (high in HL60 and HL60Rev, low in HL60AD) | Slightly up-regulated in SCC25 CDDP cell line; not significantly differentially expressed in other cell line pairs. | Slightly up-regulated in A2780AD and SCC25 CDDP cell lines; Not significantly differentially expressed in other cell line pairs. |

FIG. 6

SEQUENCE LISTING

<160> NUMBER OF SEQ ID NOS: 6

<210> SEQ ID NO 1
<211> LENGTH: 2709
<212> TYPE: DNA
<213> ORGANISM: Mus musculus

<400> SEQUENCE: 1

```
aatctttat  tttatcgatg  ttaacaagct  tagtaatcga  tgccacgtcg  agggtgtcg      60 acccacgcgt  ccgggagtag  gttgagctcg  cctgttctcc  cattgtcagc  cagtctattt     120
ccagattgtt  tgaacttctc  tggccgcaca  atacaggaag  gaagactaaa  gcagcaaagg     180
gacctacagc  gtctgcagca  tgggctggtt  aactaggatt  gtctgtcttt  tctggggagt     240
attacttaca  gcaagagcaa  actatcagaa  tgggaagaac  aatgtgccaa  ggctgaaatt     300
atcctacaaa  gaaatgttgg  aatccaacaa  tgtgatcact  ttcaatggct  tggccaacag     360
ctccagttat  cataccttcc  ttttggatga  ggaacggagt  aggctgtatg  ttggagcaaa     420
ggatcacata  ttttcattcg  acctggttaa  tatcaaggat  tttcaaaaga  ttgtgtggcc     480
agtatcttac  accagaagag  atgaatgcaa  gtgggctgga  aaagacatcc  tgaaagaatg     540
tgctaatttc  atcaaggtac  ttaaggcata  taatcagact  cacttgtacg  cctgtggaac     600
gggggctttt  catccaattt  gcacctacat  tgaaattgga  catcatcctg  aggacaatat     660
ttttaagctg  gagaactcac  attttgaaaa  cggccgtggg  aagagtccat  atgaccctaa     720
gctgctgaca  gcatcccttt  aatagatgg   agaattatac  tctggaactg  cagctgattt     780
tatggggcga  gactttgcta  tcttccgaac  tcttgggcac  caccacccaa  tcaggacaga     840
gcagcatgat  tccaggtggc  tcaatgatcc  aaagttcatt  agtgcccacc  tcatctcaga     900
gagtgacaat  cctgaagatg  acaaagtata  cttttcttc   cgtgaaaatg  caatagatgg     960
agaacactct  ggaaaagcta  ctcacgctag  aataggtcag  atatgcaaga  atgactttgg    1020
agggcacaga  agtctggtga  ataaatggac  aacattcctc  aaagctcgtc  tgatttgctc    1080
agtgccaggt  ccaaatggca  ttgacactca  ttttgatgaa  ctgcaggatg  tattcctaat    1140
gaactttaaa  gatcctaaaa  atccagttgt  atatggagtg  tttacgactt  ccagtaacat    1200
tttcaaggga  tcagccgtgt  gtatgtatag  catgagtgat  gtgagaaggg  tgttccttgg    1260
tccatatgcc  cacagggatg  gacccaacta  tcaatgggtg  ccttatcaag  gaagagtccc    1320
ctatccacgg  ccaggaactt  gtcccagcaa  acatttggt   ggttttgact  ctacaaagga    1380
ccttcctgat  gatgttataa  cctttgcaag  aagtcatcca  gccatgtaca  atccagtgtt    1440
tcctatgaac  aatcgcccaa  tagtgatcaa  acggatgta   aattatcaat  ttacacaaat    1500
tgtcgtagac  cgagtggatg  cagaagatgg  acagtatgat  gttatgttta  tcggaacaga    1560
tgttgggacc  gttcttaaag  tagtttcaat  tcctaaggag  acttggtatg  atttagaaga    1620
ggttctgctg  gaagaaatga  cagttttcg   ggaaccgact  gctatttcag  caatggagct    1680
ttccactaag  cagcaacaac  tatatattgg  ttcaacggct  ggggttgccc  agctccctt    1740 acaccggtgt  gatatttacg  ggaaagcgtg  tgctgagtgt  tgcctcgccc  gagaccctta    1800
ctgtgcttgg  gatggttctg  catgttctcg  ctattttccc  actgcaaaga  gacgcacaag    1860
acgacaagat  ataagaaatg  gagacccact  gactcactgt  tcagacttac  accatgataa    1920
tcaccatggc  cacagccctg  aagagagaat  catctatggt  gtagagaata  gtagcacatt    1980
tttggaatgc  agtccgaagt  cgcagagagc  gctggtctat  tggcaattcc  agaggcgaaa    2040
```

-continued

```
tgaagagcga aaagaagaga tcagagtgga tgatcatatc atcaggacag atcaaggcct    2100
tctgctacgt agtctacaac agaaggattc aggcaattac ctctgccatg cggtggaaca    2160
tgggttcata caaactcttc ttaaggtaac cctggaagtc attgacacag agcatttgga    2220
agaacttctt cataaagatg atgatggaga tggctctaag accaaagaaa tgtccaatag    2280
catgacacct agccagaagg tctggtacag agacttcatg cagctcatca accaccccaa    2340
tctcaacacg atggatgagt tctgtgaaca agtttggaaa agggaccgaa acaacgtcg     2400 gcaaaggcca ggacataccc cagggaacag taacaaatgg aagcacttac aagaaaataa    2460
gaaaggtaga aacaggagga cccacgaatt tgagagggca cccaggagtg tctgagctgc    2520
attacctcta gaaacctcaa acaagtagaa acttgcctag acaataactg aaaaacaaa     2580 tgcaatatac atgaactttt tcatggcat tatgtggatg tttacaatgg tgggaaattc     2640
agctgagttc caccaattat aaattaaatc catgagtaac tttcctaata ggcttttttt    2700
cctaatacc                                                            2709
```

<210> SEQ ID NO 2
<211> LENGTH: 2199
<212> TYPE: DNA
<213> ORGANISM: Mus musculus

<400> SEQUENCE: 2

```
gaattctcga gctcgtcgac cacgccctcc ttgtgcaaga actctgagcc ccaggtgcag      60
gaggctgagg cctgcagaga gacttgcaga gagacccagc aagccatggt gtttccatgg     120
agatgtgagg gtacttactg gggctcgagg aacatcctga agctgtgggt ctggacactg     180
ctctgttgtg acttcctgat acaccatgga actcactgtt ggacttacca ttattctgaa     240
aagcccatga actgggaaaa tgctagaaag ttctgcaagc aaaattacac agatttagtc     300
gccatacaaa acaagagaga aattgagtat ttagagaata cattgcccaa agcccttat      360 tactactgga taggaatcag gaaaattggg aaaatgtgga catgggtggg aaccaacaaa     420
actctcacta agaagcagag aactgggggt gctggggagc ccaacaacaa gaagtccaag     480
gaggactgtg tggagatcta tatcaagagg gaacgagact ctgggaaatg gaacgatgac     540
gcctgtcaca acgaaaggc agctctctgc tacacagcct cttgccagcc agggtcttgc      600
aatggccgtg gagaatgtgt ggaaactatc aacaatcaca cgtgcatctg tgatgcaggg    660
tattacgggc ccagtgtca gtatgtggtc cagtgtgagc ctttggaggc ccctgagttg      720
ggtaccatgg actgcatcca ccccttggga aacttcagct ccagtccaa gtgtgctttc      780 aactgttctg agggaagaga gctacttggg actgcagaaa cacagtgtgg agcatctgga     840
aactggtcat ctccagagcc aatctgccaa gtggtccagt gtgagccttt ggaggcccct     900
gagttgggta ccatggactg catccacccc ttgggaaact tcagcttcca gtccaagtgt     960
gctttcaact gttctgaggg aagagagcta cttgggactg cagaaacaca gtgtggagca    1020
tctggaaact ggtcatctcc agagccaatc tgccaagaga caaacagaag tttctcaaag   1080
atcaaagaag gtgactacaa ccccctcttc attcctgtag ccgtcatggt caccgcattc    1140
tcggggctgg catttctcat ttggctggca aggcggttaa aaaaggcaa gaaatctcaa     1200 gaaaggatgg atgatccata ctgattcatc ctttgtgaaa ggaaagccat gaagtgctaa    1260
agacaaaaca ttggaaaata acgtcaagtc ctcccgtgaa gatttacac gcaggcatct     1320 cccacattag agatgcagtg tttgctcaac gaatctggaa ggatttcttc atgaccaaca    1380
```

-continued

```
gctcctcccta atttcccctc gctcattcat cccattaacc ctatcccata atgtgtgtct    1440
atacagagta gtattttatc atcttttctg tggaggaaca agcaaaagtg ttactgtaga    1500
atataaagac agctgctttt actctttcct aactcttgtt tcctagttca attcagcaca    1560
gaagctaatg ccaaacacag tgaaaatatg atccatgagt aattggaaac tcagactcct    1620
tgcgcatagt acgtacccta tgtaacatcg acaaaaatct ttcatttcca cctccaaaga    1680
acagtgctct attcaagttg ggaaagtcct acttcctctg tagacccact atctgtgagt    1740
gacagccact gtagctgttc acattaacct tccccatctc cttttcctag gagaataatt    1800
ccacacactg caccccatga tggccaccaa acatcaaaga agggaaaatc tcctgcattg    1860
agttttagtt ttgagttttc ccttctcttt attagatctc tgatggttcc ttgaagtcag    1920
tgttctgatg attattaata gttaatgata acacaaccca ctctcttgga gctgatgtta    1980
tgaagacaac aggtagaaaa attcctgggc tcaggctgga gtgacaccct tttctttccc    2040
taacatcttc tactcagata cctaaattta agattcagga cagctgtccc caactcttac    2100
catgtctttt ataacttgct ccttaacttg cccaacctgt aggctatctc attttctcgc    2160
ttcactctgc aaggtttata acatgatgaa tttaaatac                           2199
```

<210> SEQ ID NO 3  
<211> LENGTH: 807  
<212> TYPE: DNA  
<213> ORGANISM: Mus musculus

<400> SEQUENCE: 3

```
gtcgacccac gcgtccgcag acctagtagc tgtggaaacc atggccctga gtgtcatgtg     60
tctgggcctt gccctgcttg gggtcctgca gagccaggcc caggactcaa ctcagaactt    120
gatccctgcc ccatctctgc tcactgtccc cctgcagcca gacttccgga gcgatcagtt    180
ccggggcagg tggtacgttg tgggcctggc aggcaatgcg gtccagaaaa aaacagaagg    240
cagctttacg atgtacagca ccatctatga gctacaagag aacaatagct acaatgtcac    300
ctccatcctg gtcagggacc aggaccaggg ctgtcgctac tggatcagaa catttgttcc    360
aagctccagg gctggccagt tcactctggg aaatatgcac aggtatcctc aggtacagag    420
ctacaatgtg caagtggcca ccacggacta caaccagttc gccatggtat ttttccgaaa    480
gacttctgaa acaagcaat acttcaaaat taccctgtat ggaagaacca aggagctgtc    540
ccctgaactg aaggaacgtt tcacccgctt tgccaagtct ctgggcctca aggacgacaa    600
catcatcttc tctgtctgtc tgccactcca tctttcctgt tgccagagag ccacctggct    660
gccccaccag ccaccatacc aaggagcatc tggagcctct tcttatttgg ccagcactcc    720
ccatccacct gtcttaacac caccaatggc gtccccttc tgctgaataa atacatgccc    780
ccaaaaaaaa aaaaaaggg cggccgc                                        807
```

<210> SEQ ID NO 4  
<211> LENGTH: 241  
<212> TYPE: PRT  
<213> ORGANISM: Mus musculus

<400> SEQUENCE: 4

```
Met Ala Leu Ser Val Met Cys Leu Gly Leu Ala Leu Leu Gly Val Leu
 1               5                  10                  15

Gln Ser Gln Ala Gln Asp Ser Thr Gln Asn Leu Ile Pro Ala Pro Ser
             20                  25                  30
```

```
Leu Leu Thr Val Pro Leu Gln Pro Asp Phe Arg Ser Asp Gln Phe Arg
         35                  40                  45

Gly Arg Trp Tyr Val Val Gly Leu Ala Gly Asn Ala Val Gln Lys Lys
 50                  55                  60

Thr Glu Gly Ser Phe Thr Met Tyr Ser Thr Ile Tyr Glu Leu Gln Glu
65                  70                  75                  80

Asn Asn Ser Tyr Asn Val Thr Ser Ile Leu Val Arg Asp Gln Asp Gln
                 85                  90                  95

Gly Cys Arg Tyr Trp Ile Arg Thr Phe Val Pro Ser Arg Ala Gly
            100                 105                 110

Gln Phe Thr Leu Gly Asn Met His Arg Tyr Pro Gln Val Gln Ser Tyr
            115                 120                 125

Asn Val Gln Val Ala Thr Thr Asp Tyr Asn Gln Phe Ala Met Val Phe
130                 135                 140

Phe Arg Lys Thr Ser Glu Asn Lys Gln Tyr Phe Lys Ile Thr Leu Tyr
145                 150                 155                 160

Gly Arg Thr Lys Glu Leu Ser Pro Glu Leu Lys Glu Arg Phe Thr Arg
                165                 170                 175

Phe Ala Lys Ser Leu Gly Leu Lys Asp Asp Asn Ile Ile Phe Ser Val
            180                 185                 190

Cys Leu Pro Leu His Leu Ser Cys Cys Gln Arg Ala Thr Trp Leu Pro
            195                 200                 205

His Gln Pro Pro Tyr Gln Gly Ala Ser Gly Ala Ser Ser Tyr Leu Ala
210                 215                 220

Ser Thr Pro His Pro Pro Val Leu Thr Pro Pro Met Ala Ser Pro Phe
225                 230                 235                 240

Cys

<210> SEQ ID NO 5
<211> LENGTH: 1400
<212> TYPE: DNA
<213> ORGANISM: Mus musculus

<400> SEQUENCE: 5 cccctttgg tttttgttct atcgacccta acaagcttag taatcgatgc cactcgaggc      60
caagaattca ttacgagcct gagctccttc ggctttttcc cccctttgc atcttgtttc     120
ccgggatacc tgcaactcaa ggatggatgc cctgagactg gcaaattcag cttttgctgt    180
tgacttgttc aaacaactat gtgaaaggga cccagcagga acattctct tctctccaat     240
atgcctctct acttctctgt cccttgcgca agtgggcacc aaaggcgaca cagcaaatga    300
aattggacag gtccttcatt ttgagaatgt caaagatgta ccctttgggt ttcaaacagt    360
cacttctgat gttaataagc tcagttcttt ttactctttg aaacttgtca agcgactcta    420
catagacaaa tctctgaacc cttctacaga atttatcagt tctaccaaaa gaccatatgc    480
aaaagaattg gaaactgttg acttcaaaga caaactggaa gaaacgaaag gtcaaattaa    540
cagctccatt aaggagctca gatggccca ctttgaggac atttttgtcag agaacagtat    600
aagtgaccag accaaaatcc ttgtggttaa tgctgcctac tttgttggaa agtggatgaa    660
gaaatttccg gaatcagaaa caaagaatg tcctttcaga atcagcaaga cagacaccaa    720
acccgtacaa atgatgaatc ttgaggccac tttctgcttg ggtaacattg atgacatcag    780
ctgtaagatc atagaacttc ctttccagaa taagcatctg agtatgctca ttgtgctccc    840
caaggacgtg gaggatgagt ccacaggcct ggagaagatt gaacagcaac tcaacccaga    900
```

-continued

```
aacattgtta cagtggacca accccagtac catggccaat gccaaagtca aactttccct      960
cccaaagttt aaggtagaaa agatgattga tcccaaggct agtctggaaa gcctagggct     1020
gaaaagtctc ttcaatgaaa gtacatcgga tttctctgga atgtcagaga ccaagggagt     1080
gtccctgtca aatgtgattc atagagtatg cctagaaata accgaagatg gtggtgagtc     1140
catcgaggtg ccagggtccc ggatcttaca gcacaaggga gaattcaatg ctgaccatcc     1200
atttatttat atcattagac acaacaaaac tcgaaacatc attttctttg caaattctg      1260 ttctccttag ctggcagggc cttgccaagt ctcaggaac ttgtctgtag tcgcagagct      1320
ctgtaaactt tgtatccaga caatcacttt ctatacaata aattgtaaat gttgctgaaa     1380
aaaaaaaaaa aaaaaaaaa                                                  1400

<210> SEQ ID NO 6
<211> LENGTH: 2137
<212> TYPE: DNA
<213> ORGANISM: Homo sapiens

<400> SEQUENCE: 6
ggtggagact aaatataatc ttttatttta tcgatgttaa caagcttagt aatcgatgcc       60
acgtcgaggg gtgtcgaccc acgcgtctcg cttgcctgtt ccttttccac gcattttcca      120
ggataactgt gactccaggc ccgcaatgga tgccctgcaa ctagcaaatt cggcttttgc      180
cgttgatctg ttcaaacaac tatgtgaaaa ggagccactg gcaatgtcc tcttctctcc       240 aatctgtctc tccacctctc tgtcacttgc tcaagtgggt gctaaaggtg acactgcaaa      300
tgaaattgga caggttcttc attttgaaaa tgtcaaagat gtacccttg gatttcaaac       360 agtaacatcg gatgtaaaca aacttagttc cttttactca ctgaaactaa tcaagcggct      420
ctacgtagac aaatctctga atctttctac agagttcatc agctctacga agagaccccta    480 tgcaaaggaa ttggaaactg ttgacttcaa agataaattg gaagaaacga aggtcagat      540 caacaactca attaaggatc tcacagatgg ccactttgag aacattttag ctgacaacag     600
tgtgaacgac cagaccaaaa tccttgtggt taatgctgcc tactttgttg gcaagtggat     660
gaagaaattt cctgaatcag aaacaaaaga atgtcctttc agagtcaaca agacagacac    720
caaaccagtg cagatgatga acatggaggc cacgttctgt atgggaaaca ttgacagtat    780
caattgtaag atcatagagc ttccttttca aaataagcat ctcagcatgt tcatcctact     840
acccaaggat gtggaggatg agtccacagg cttggagaag attgaaaaac aactcaactc     900
agagtcactg tcacagtgga ctaatcccag caccatggcc aatgccaagg tcaaactctc     960
cattccaaaa tttaaggtgg aaaagatgat tgatcccaag gcttgtctgg aaaatctagg    1020
gctgaaacat atcttcagcg aagacacatc tgatttctct ggaatgtcag agaccaaggg    1080
agtggcccta tcaaatgtta tccacaaagt gtgcttagaa ataactgaag atggtgggga    1140
ttccatagag gtgccaggag cacggatcct gcagcacaag gatgaattga atgctgacca    1200
tccctttatt tacatcatca ggcacaacaa aactcgaaac atcattttct ttggcaaatt    1260
ctgttctcct taagtggcat agcccatgtt aagtcctccc tgactttct gtggatgccg    1320 atttctgtaa actctgcatc cagagattca ttttctagat acaataaatt gctaatgttg     1380
ctggatcagg aagccgccag tacttgtcat atgtagcctt cacacagata gaccttttt     1440 ttttttttcca attctatctt ttgtttcctt ttttcccata agacaatgac atacgctttt    1500
aatgaaaagg aatcacgtta gaggaaaaat atttattcat tatttgtcaa attgtccggg    1560
```

-continued

```
gtagttggca gaaatacagt cttccacaaa gaaaattcct ataaggaaga tttggaagct    1620
cttcttccca gcactatgct ttccttcttt gggatagaga atgttccaga cattctcgct    1680
tccctgaaag actgaagaaa gtgtagtgca tgggacccac gaaactgccc tggctccagt    1740
gaaacttggg cacatgctca ggctactata ggtccagaag tccttatgtt aagccctggc    1800
aggcaggtgt ttattaaaat tctgaatttt ggggattttc aaaagataat atttacata    1860 cactgtatgt tatagaactt catggatcag atctggggca gcacccata aatcaccacc    1920 ttaatatgct gcaacaaaat gtagaatatt cagacaaaat ggatacataa agactaagta    1980
gcccataagg ggtcaaattt tgctgccaaa tgcgtatgcc accaacttac aaaaacactt    2040
cgttcgcaga gcttttcaga ttgtggaatg ttggataagg aattatagac ctctagtagc    2100
tgaaatgcaa gaccccaaga ggaagttcag atcttaa                              2137
```

RESISTANCE SEQUENCES AND USES THEREOF

RELATED APPLICATION INFORMATION

This application claims priority from provisional application Ser. No. 60/179,191, filed Jan. 31, 2000.

BACKGROUND

The invention relates to chemotherapy and drug resistance.

Cancer chemotherapy commonly involves the administration of one or more cytotoxic or cytostatic drugs to a patient. The goal of chemotherapy is to eradicate a substantially clonal population (tumor) of transformed cells from the body of the individual, or to suppress or to attenuate growth of the tumor. Tumors may occur in solid or liquid form, the latter comprising a cell suspension in blood or other body fluid. A secondary goal of chemotherapy is stabilization (clinical management) of the afflicted individual's health status. Although the tumor may initially respond to chemotherapy, in many instances the initial chemotherapeutic treatment regimen becomes less effective or ceases to impede tumor growth. The selection pressure induced by chemotherapy promotes the development of phenotypic changes that allow tumor cells to resist the cytotoxic effects of a chemotherapeutic drug.

SUMMARY

The present invention concerns sequences whose expression is increased or decreased in drug resistant tumor cells (drug resistance sequences) compared to non-drug resistant or less drug resistant tumor cells. Expression of the resistance sequences is either increased (up-regulated sequences) or decreased (down-regulated sequences) in a particular tumor cell (i.e., drug-resistant EMT-6 cell) when compared to expression in a control cell (i.e., non-drug resistant EMT-6). Drug resistance sequences include nucleic acids and polypeptides that are useful in, for example, diagnostic methods related to identification of drug resistant cells (e.g., cancer cells). Resistance sequences (i.e., resistance genes, resistance mRNAs, resistance cDNAs, resistance polypeptides, and resistance proteins) are also useful in screening methods directed to the identification of compounds that can modulate (increase or decrease) the drug resistance of a particular cell type or multiple cell types.

The resistance sequences of the invention include semaphorin D (e.g., Genbank Accession No.: X85993 and SEQ ID NO:1; see FIG. 1) and semaphorin III (e.g., Genbank Accession No.: L26081), B94 (e.g., Genbank Accession No: L24118 and Genbank Accession No.: M92357), mel-14 antigen (e.g., Genbank Accession No.: M25324 and SEQ ID NO:2; see FIG. 2; and Genbank Accession No.: M25280), 24p3 (e.g., Genbank Accession No.: W13166; Genbank Accession No.: X81627; SEQ ID NOS:3 and 4; see FIG. 3), proliferin (e.g., Genbank Accession No.: K03235), and maspin (e.g., Genbank Accession No.: U54705; Genbank Accession No. U04313; and SEQ ID NOS:5 and 6, see FIG. 4 and FIG. 5).

The resistance polypeptides and proteins of the present invention, or portions thereof, e.g., a biologically active portion, can be operatively linked to a non-resistance polypeptide (e.g., heterologous amino acid sequences) to form a resistance fusion protein. The invention further features antibodies (monoclonal or polyclonal) that specifically bind a resistance polypeptide or protein. In addition, a resistance protein (a protein encoded by a resistance gene) or biologically active portions thereof can be incorporated into a pharmaceutical composition, which optionally include pharmaceutically acceptable carriers.

In another aspect, the present invention provides a method for detecting the presence of resistance activity or expression in a biological sample by contacting the biological sample with an agent capable of detecting an indicator of a resistance sequence activity such that the presence of the activity is detected in the biological sample. For example, the invention includes a method for detecting the presence of a resistance polypeptide in a sample. This method features the steps of contacting the sample with a compound which selectively binds to the polypeptide and then determining whether the compound binds to a polypeptide in the sample. In some cases, the compound which binds to the polypeptide is an antibody. The invention also features methods for detecting the presence of a resistance mRNA (an mRNA encoding a resistance protein in a sample). This method includes the steps of contacting the sample with a nucleic acid probe or primer which selectively hybridizes to a resistance mRNA; and then determining whether the nucleic acid probe or primer binds to a nucleic acid molecule in the sample.

In another aspect, the invention provides a method for modulating the activity of a resistance protein comprising contacting a cell with an agent that modulates (inhibits or stimulates) activity of the resistance protein or expression such that resistance activity or expression in the cell is modulated. In one embodiment, the agent is an antibody that specifically binds to a resistance protein. In another embodiment, the agent modulates resistance expression by modulating transcription of a gene encoding a resistance protein, splicing of a resistance mRNA, or translation of a resistance mRNA. In yet another embodiment, the agent is a nucleic acid molecule having a nucleotide sequence that is antisense to the coding strand of a resistance mRNA or a gene encoding a resistance protein.

In one embodiment, the methods of the present invention are used to treat a subject having a disorder (e.g., a drug-resistant cancer) characterized by aberrant resistance sequence expression (e.g., of a protein or nucleic acid) or activity by administering to the subject an agent which is a resistance modulator. In one embodiment, the resistance modulator is a resistance protein. In another embodiment the resistance modulator is a resistance nucleic acid molecule. In other embodiments, the resistance modulator is a peptide, peptidomimetic, or other small molecule.

The present invention also provides a diagnostic assay for identifying the presence or absence of a genetic lesion or mutation characterized by at least one of: (i) aberrant modification or mutation of a gene encoding a resistance protein; (ii) mis-regulation of a gene encoding a resistance protein; (iii) aberrant RNA splicing; and (iv) aberrant post-translational modification of a resistance protein, wherein a wild-type form of the gene encodes a protein with a resistance activity.

The invention also features methods for identifying a compound which modulates expression of a resistance nucleic acid or polypeptide. In general, such methods involve measuring resistance expression in the presence and absence of a test compound and identifying those compounds which alter the resistance expression. The resistance expression that is measured can be expression of a resistance nucleic acid or a resistance polypeptide.

Also within the invention are kits that include a compound which selectively binds to a resistance polypeptide or nucleic acid and instructions for use. Such kits can be used to determine whether a particular cell type or cells within a biological sample, e.g., a sample of patient cells, are drug resistant.

The invention features methods for identifying a compound which binds to a resistance polypeptide. These methods include the steps of contacting a resistance polypeptide with a test compound and then determining whether the polypeptide binds to the test compound. In various embodiments of these methods, the binding of the test compound to the resistance polypeptide is detected using an assay which measures binding of the test compound to the polypeptide or using a competition binding assay.

The invention also includes a method for modulating the activity of a resistance polypeptide. This method includes the steps of contacting the polypeptide or a cell expressing the polypeptide with a compound which binds to the polypeptide in a sufficient concentration to modulate the activity of the polypeptide.

In another aspect, the invention provides a method for identifying a compound that modulates the activity of a resistance polypeptide (e.g., an up-regulated protein or a down-regulated protein). In general, such methods entail measuring a biological activity of the polypeptide in the presence and absence of a test compound and identifying those compounds which alter the activity of the polypeptide. One such method includes the steps of contacting the polypeptide with a test compound and then determining the effect of the test compound on the activity of the polypeptide to thereby identify a compound which modulates the activity of the polypeptide.

Other aspects of the invention are methods and compositions relating to drug resistance. A "drug-resistant phenotype" refers to a cellular phenotype which is associated with increased survival after exposure to a particular dose of a drug, e.g., a chemotherapeutic drug, compared to a cell that does not have this phenotype. A "drug-resistant cell" refers to a cell that exhibits this phenotype. Drug resistance commonly occurs as multi-drug resistance (multiple drug resistance) in which a cell population or tumor becomes relatively resistant to a drug to which it has been exposed as well as to other drugs to which it has not been exposed.

A cell that exhibits drug resistance can be characterized by lower intracellular concentration of a drug compared to a non-resistant cell or a less resistant cell as well as altered ability of a drug to affect its target compared to a non-resistant cell or a less resistant cell. Drug resistance is described in detail by Hochhauser and Harris ((1991) *Brit. Med. Bull.* 47:178–96); Simon and Schindler ((1994) *Proc. Nat'l Acad Sci USA* 91: 3497–504); and Harris and Hochhauser ((1992) *Acta Oncologica* 31:205–213); Scotto et al. ((1986) *Science* 232:751–55). Multi-drug resistance can be associated with, for example, altered composition of plasma membrane phospholipids; increased drug binding and intracellular accumulation; altered expression or activity of plasma membrane or endomembrane channels, transporters or translocators; altered rates of endocytosis and associated alteration in targeting of endosomes; altered exocytosis; altered intracellular ionic environments; altered expression or activity of proteins involved in drug detoxification; and altered expression or activity of proteins involved in DNA repair or replication.

Also within the invention is a method of determining whether a cell has a drug-resistant phenotype by measuring the expression or activity of a drug resistance sequence (e.g., an mRNA or a polypeptide) in the cell and comparing this expression or activity to expression or activity in a control cell. The drug resistance sequence can be an mRNA ("resistance mRNA") or a polypeptide ("resistance protein").

Increased expression or activity of an up-regulated resistance sequence or its product in the cell compared to the control cell indicates that the cell has a drug-resistant phenotype.

Decreased expression or activity of a down-regulated resistance sequence or its product in the cell compared to the control cell indicates that the cell has a drug-resistant phenotype.

In one embodiment of this method, drug resistance is determined by measuring a drug resistance sequence (e.g., measuring an up-regulated resistance protein such as semaphorin D, B94, mel-14, 24p3, or proliferin; or a down-regulated resistance protein such as maspin, using an antibody directed against the protein). In another embodiment, resistance sequence expression is measured by quantifying mRNA encoding a resistance protein or the copy number of the gene encoding the resistance protein. In another embodiment resistance sequence activity is measured using any assay which can quantify a biological activity of a resistance protein.

The invention also includes a method for modulating the drug resistance of a cell by modulating resistance expression or activity within the cell. Thus in one embodiment, the drug resistance of a cell is reduced by contacting the cell with a molecule (e.g., an antisense nucleic acid molecule) that reduces the expression of an up-regulated resistance sequence within the cell. In another embodiment, drug resistance of a cell is reduced by increasing expression of a down-regulated resistance sequence within the cell.

Another aspect of the present invention is a method of improving effectiveness of chemotherapy for a mammal having a disorder associated with the presence of drug-resistant neoplastic cells. In this method, a chemotherapeutic drug and a molecule that reduces expression of an up-regulated resistance sequence or increases expression of a down-regulated resistance sequence can be co-administered to a mammal. The invention also includes a method of identifying a compound that modulates the drug resistance of a cell by first contacting the cell with a test compound and then measuring and comparing expression of a resistance sequence in the cell exposed to the compound to expression of the resistance sequence in a control cell not exposed to the compound. The compound is identified as modulator of drug resistance when the level of expression of the resistance sequence in the cell exposed to the compound differs from the level of expression of the resistance sequence in a cell not exposed to the compound. In one embodiment of this method, the cell has a drug-resistant phenotype. In another embodiment, the cell is a mammalian cell. This method may also include an optional step of measuring the drug resistance of the cell in the presence of the identified modulator of drug resistance. The compounds modulating resistance that are identified in the foregoing methods are also included within the invention.

The invention also features a method of treating a mammal suspected of having a disorder associated with the presence of drug-resistant cells. This method includes the steps of determining whether a mammal has a disorder associated with the presence of drug-resistant cells (e.g., drug-resistant cancer), and administering to the mammal a compound that sufficiently alters expression of, e.g., an up-regulated resistance sequence, so that the drug resistance of the cells associated with the disorder is modulated (i.e., reduced). In the case of a down-regulated resistance sequence, the compound administered to the mammal increases expression of the sequence thereby modulating (i.e., reducing) drug resistance.

Another feature of the invention is a method for treating a patient having a neoplastic disorder (e.g., cancer) by administering to the patient a therapeutically effective amount of a compound that alters the expression of a resistance sequence.

In the context of cancer treatment, the expression level of a resistance sequence may be used to: 1) determine if a cancer, particularly a drug resistant cancer, can be treated by an agent or combination of agents; 2) determine if a cancer is responding to treatment with an agent or combination of agents; 3) select an appropriate agent or combination of agents for treating a cancer; 4) monitor the effectiveness of an ongoing treatment; and 5) identify new cancer treatments (either single agent or combination of agents). In particular, a resistance sequence may be used as a marker (surrogate and/or direct) to determine appropriate therapy, to monitor clinical therapy and human trials of a drug being tested for efficacy, and in developing new agents and therapeutic combinations.

Accordingly, the present invention provides methods for determining whether an agent, e.g., a chemotherapeutic agent such as CDDP (cisplatin) or CTX (Cytoxan), will be effective in reducing the growth rate of cancer cells comprising the steps of: a) obtaining a sample of cancer cells; b) determining the level of expression in the cancer cells of a resistance sequence; and c) identifying that an agent will be effective when the resistance sequence is expressed at a level not associated with drug resistance (e.g., an up-regulated resistance sequence is not expressed or is expressed at relatively low level compared to a non-drug resistant cancer cell; a down-regulated resistance sequence may be expressed at a relatively high level). Alternatively, in step (c), an agent can be identified as being relatively ineffective for treating the cancer when a resistance sequence is expressed at a level associated with resistance to that agent (e.g., an up-regulated resistance sequence at a relatively high level compared to a non-drug resistant cell or a down-regulated resistance sequence can be expressed at a relatively low level).

As used herein, an agent is said to reduce the rate of growth of cancer cells when the agent can reduce at least 50%, preferably at least 75%, most preferably at least 95% of the growth of the cancer cells. Such inhibition can further include a reduction in survivability and an increase in the rate of death of the cancer cells. The amount of agent used for this determination will vary based on the agent selected. Typically, the amount will be a predefined therapeutic amount.

As used herein, an agent is defined broadly as anything that cancer cells can be exposed to in a therapeutic protocol. In the context of the present invention, such agents include, but are not limited to, chemotherapeutic agents, such as anti-metabolic agents, e.g., Ara AC, 5-FU and methotrexate; antimitotic agents, e.g., Taxol, vinblastin and vincristine; alkylating agents, e.g., melphanlan, BCNU, cyclophosphamide, and nitrogen mustard; topoisomerase II inhibitors, e.g., VW-26, topotecan and Bleomycin; strand-breaking agents, e.g., doxorubicin and DHAD; cross-linking agents, e.g., cisplatin, CBDCA, radiation and ultraviolet light.

The agents tested in the present methods can be a single agent or a combination of agents. For example, the present methods can be used to determine whether a single chemotherapeutic agent, such as methotrexate, can be used to treat a cancer or whether a combination of two or more agents can be used.

Cancer cells include, but are not limited to, carcinomas, such as squamous cell carcinoma, basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, seminoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; leukemias and lymphomas such as granulocytic leukemia, monocytic leukemia, lymphocytic leukemia, malignant lymphoma, plasmocytoma, reticulum cell sarcoma, or Hodgkins disease; and tumors of the nervous system including glioma, meningioma, medulloblastoma, schwannoma or epidymoma.

The source of the cancer cells used in the methods of the invention will be based on how the method of the present invention is being used. For example, if the method is being used to determine whether a patient's cancer can be treated with an agent, or a combination of agents, then the preferred source of cancer cells will be cancer cells obtained from a cancer biopsy from the patient. Alternatively, cancer cells line of similar type to that being treated can be assayed. For example if breast cancer is being treated, then a breast cancer cell line can be used. If the method is being used to monitor the effectiveness of a therapeutic protocol, then a tissue sample from the patient being treated is the preferred source. If the method is being used to identify new therapeutic agents or combinations, then any cancer cells, e.g., cells of a cancer cell line, can be used.

A skilled artisan can readily select and obtain the appropriate cancer cells that are used in the present method. For example, the EMT-6 cancer cell lines, used in the examples, can be made using the method described by Teicher et al. (1990) Science 247:1457–1461). For cancer cells obtained from a patient, standard biopsy methods, such as a needle biopsy, can be employed.

In the methods of the present invention, the level or amount of expression of a resistance sequence is determined. As used herein, the level or amount of expression refers to the absolute level of expression of an resistance mRNA or the absolute level of expression of a resistance protein (i.e., whether or not expression is occurring in the cancer cells).

As an alternative to making determinations based on the absolute expression level of selected genes, determinations may be based on the normalized expression levels. Expression levels are normalized by correcting the absolute expression level of a sensitivity or resistance sequence by comparing its expression to the expression of a sequence that is not a sensitivity or resistance sequence, e.g., a sequence encoded by housekeeping gene that is constitutively expressed. Suitable genes for normalization include housekeeping genes such as the actin gene. This normalization allows one to compare the expression level in one sample, e.g., a patient sample, to another sample, e.g., a non-cancer sample, or between samples from different sources. Alternatively, the expression level can be provided as a relative expression level. To determine a relative expression level of a gene, the level of expression of the gene is determined for 10 or more samples, preferably 50 or more samples, prior to the determination of the expression level for the sample in question. The mean expression level of the gene assayed in the larger number of samples is determined and this is used as a baseline expression level for the gene in question. The expression level of the gene determined for the test sample (absolute level of expression) is then divided by the mean expression value obtained for that gene. This provides a relative expression level and aids in identifying extreme cases of sensitivity or resistance. Preferably, the samples used will be from similar tumors or from non-cancerous cells of the same tissue origin as the tumor in question. The choice of the cell source is dependent on the use of the relative expression level data. For example, using tumors of similar types for obtaining a mean expression score allows for the identification of extreme cases of sensitivity or resistance. Using expression found in normal tissues as a mean expression score aids in validating whether the gene assayed is tumor specific (versus normal cells).

Also within the invention is a method for increasing drug resistance in a cell by altering the level of expression of a resistance sequence by administering a compound that alters the expression of the resistance sequence. For example, drug resistance may be increased by increasing the expression of an up-regulated sequence in the cell. Decreasing expression of a down-regulated sequence can increase drug resistance. Such methods are useful for the protection of non-neoplastic cells during chemotherapy.

The invention features a method for determining whether a test compound modulates the drug resistance of a cell, the method including: a) determining the level of expression of a resistance sequence (e.g., a resistance protein encoded by an endogenous or heterologous gene) in a cell in the presence of a test compound; b) determining the level of expression of the resistance sequence in the cell in the absence of the test compound; and c) identifying the compound as a modulator of drug resistance of the cell if the level of expression of the resistance sequence in the cell in the presence of the test compound differs from the level of expression of the resistance sequence in the cell in the absence of the test compound.

The invention also features a method for determining whether a test compound modulates the drug resistance of a cell, the method including: a) incubating a resistance protein in the presence of a test compound; b) determining whether the test compound binds to the resistance protein; c) selecting a test compound which binds to the resistance protein; d) administering the test compound selected in step c) to a non-human mammal having drug resistant cells; e) determining whether the test compound alters the drug resistance of the cells in the non-human mammal; and f) identifying the test compound as a modulator of drug resistance of the cell if the compound alters the drug resistance of the cells in step e).

The invention further features a method for determining whether a test cell has a drug-resistant phenotype, the method including: a) measuring the expression of a resistance sequence in the test cell; b) comparing the expression of the resistance sequence measured in step a) to the expression of the resistance sequence in a control cell not having a drug-resistant phenotype; and c) determining that the test cell has a drug resistant phenotype if the expression of the resistance sequence in the test cell is greater than the expression of the resistance sequence in the control cell when the resistance sequence is an up-regulated sequence. In another embodiment of this aspect of the invention, the test cell of step (c) may have a drug resistant phenotype if the expression of the resistance sequence in the test cell is lower than the expression of the resistance sequence in the control cell when the resistance sequence is a down-regulated sequence.

In another aspect the invention features a method of determining whether a test cell has a drug-resistant phenotype, the method including: a) measuring the activity of a resistance sequence in the test cell; b) comparing the activity of the resistance sequence measured in step a) to the activity of the resistance sequence in a control cell not having a drug-resistant phenotype; and c) determining that the test cell has a drug resistant phenotype if the activity of the resistance sequence in the test cell is greater than the activity of the resistance sequence in the control cell when the resistance sequence is an up-regulated sequence. In another embodiment, the test cell of step (c) has a drug resistant phenotype if the activity of the resistance sequence in the test cell is less than the activity of the resistance sequence in the control cell when the resistance sequence is a down-regulated sequence.

In yet another aspect the invention features a method for determining whether a subject has or is at risk of developing a drug resistant tumor, the method including: a) measuring the expression of resistance sequence (e.g., mRNA encoding a resistance protein) in a biological sample obtained from the subject (using, e.g., a nucleic acid molecule that hybridizes to the mRNA); b) comparing the expression of the mRNA measured in step a) to the expression of the mRNA in a biological sample obtained from a control subject not having a drug resistant tumor; and c) determining that the patient has or is at risk of developing a drug resistant tumor if the expression of the mRNA in the biological sample obtained from the patient is higher than the expression of the mRNA in the biological sample obtained from the control subject when the resistance mRNA is an up-regulated sequence. In another embodiment, the patient has or is at risk of developing a drug resistant tumor if the expression of the resistance mRNA in the biological sample obtained from the patient is lower than the expression of the mRNA in the biological sample obtained from the control subject when the mRNA is a down-regulated sequence.

In still another aspect the invention features a method for determining whether a subject has or is at risk of developing a drug resistant tumor, the method including: a) measuring the activity of a resistance sequence in a biological sample obtained from the subject (using, e.g., an agent that binds to the resistance protein); b) comparing the activity of the resistance measured in step a) to the expression of the resistance sequence in a biological sample obtained from a control subject not having a drug resistant tumor; and c) determining that the patient has or is at risk of developing a drug resistant tumor if the activity of the resistance sequence in the biological sample obtained from the patient is higher than the activity of the resistance sequence in the biological sample obtained from the control subject when the resistance sequence is an up-regulated sequence. In another embodiment, the patient has or is at risk of developing a drug resistant tumor if the activity of the resistance sequence in the biological sample obtained from the patient is lower than the activity of the resistance sequence in the biological sample obtained from the control subject when the resistance sequence is a down-regulated sequence.

The invention also features a method for monitoring the effect of an anti-tumor treatment on a patient, the method including: a) measuring the expression of a resistance sequence in a tumor sample obtained from the patient (using, e.g., a nucleic acid molecule that hybridizes to the resistance mRNA); b) comparing the expression of the resistance sequence measured in step a) to the expression of the resistance sequence in a control sample of cells; and c) determining that the anti-tumor treatment should be discontinued or modified if the expression of the resistance sequence in the tumor sample is higher than the expression of resistance sequence in the control sample of cells when the resistance sequence is an up-regulated sequence. In another embodiment, the anti-tumor treatment should be discontinued or modified as in step (c) if the expression of the resistance sequence in the tumor sample is lower than the expression of the resistance sequence in the control sample of cells when the resistance sequence is a down-regulated sequence.

The invention also features a method for monitoring the effect of an anti-tumor treatment on a patient, the method including: a) measuring the activity of a resistance sequence in a tumor sample obtained from the patient (using, e.g., an agent that binds to the resistance protein); b) comparing the activity of the resistance sequence measured in step a) to the activity of the resistance sequence in a control sample of cells; and c) determining that the anti-tumor treatment should be discontinued or modified if the activity of the resistance sequence in the tumor sample is higher than the activity of the resistance sequence in the control sample of cells when the resistance sequence is an up-regulated sequence. In another embodiment, it is determined that the anti-tumor treatment should be discontinued or modified as in step (c) if the activity of the resistance sequence in the tumor sample is lower than the activity of the resistance sequence in the control sample of cells when the resistance sequence is a down-regulated sequence.

The invention further features a method for modulating the drug resistance of a cell by modulating expression of a resistance sequence within the cell and a method for reducing the drug resistance of cell by contacting the cell with a molecule which reduces the expression of the resistance sequence within the cell when the resistance sequence is an up-regulated sequence. In another embodiment, the invention features a method for modulating the drug resistance of a cell by modulating expression of a resistance sequence within the cell and a method for reducing the drug resistance of cell by contacting the cell with a molecule which increases the expression of the resistance sequence within the cell when the resistance sequence is a down-regulated sequence.

The invention also features a method of increasing the effectiveness of a chemotherapeutic compound in a patient suffering from a disorder associated with the presence of drug-resistant neoplastic cells, the method including: a) administering a chemotherapeutic compound to the patient; and b) administering a compound which reduces the expression of an up-regulated resistance sequence in the patient. The invention further features a method of increasing the effectiveness of a chemotherapeutic compound in a patient suffering from a disorder associated with the presence of drug-resistant neoplastic cells, the method including: a) administering a chemotherapeutic compound to the patient; and b) administering a compound which reduces the expression of a down-regulated resistance sequence in the patient.

The invention features a method of treating a mammal suspected of having a disorder associated with the presence of drug-resistant cells, the method including administering to the mammal a compound that reduces the expression of a resistance sequence in the drug-resistant cells, the reduction being sufficient to reduce the drug resistance of the drug resistant cells when the resistance sequence is an up-regulated resistance sequence. In another embodiment, the invention features a method of treating a mammal suspected of having a disorder associated with the presence of drug-resistant cells, the method including administering to the mammal a compound that increases the expression of a resistance sequence in the drug-resistant cells, the reduction being sufficient to reduce the drug resistance of the drug resistant cells when the resistance sequence is a down-regulated resistance sequence.

The invention also features a method for increasing the drug resistance of cell that has an undesirably low level of expression of a resistance sequence, the method including exposing the cell to a compound that increases the expression of the resistance sequence when the resistance sequence is an up-regulated resistance sequence. In another embodiment, the invention features a method for increasing the drug resistance of cell that has an undesirably high level of expression of a resistance sequence, the method including exposing the cell to a compound that decreases the expression of the resistance sequence when the resistance sequence is a down-regulated resistance sequence.

The invention also features a method for treating a drug resistant tumor in a patient, the method comprising administering to said subject an amount of a resistance sequence antagonist or agonist effective to reduce drug resistance of said tumor in the patient. In another aspect, the invention features the use of an inhibitor of expression of a resistance sequence, or pharmaceutically acceptable salt thereof, or a pharmaceutical composition containing either entity, for the manufacture of a medicament for the treatment of a drug resistant tumor in a patient.

Unless otherwise defined, all technical and scientific terms used herein have the same meaning as commonly understood by one or ordinary skill in the art to which this invention belongs. Although methods and materials similar or equivalent to those described herein can be used in the practice or testing of the present invention, the preferred methods and materials are described herein. All publications, patent applications, patents, and other references mentioned herein are incorporated by reference in their entirety. In addition, the materials, methods, and examples are illustrative only and are not intended to be limited. Other features and advantages of the invention will be apparent from the detailed description and from the claims.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 1A–1B depict a nucleotide sequence of a cDNA encoding semaphorin D (SEQ ID NO:1).

FIGS. 2A–2B depict a nucleotide sequence of a cDNA encoding a mel-14 antigen (SEQ ID NO:2).

FIG. 3A depicts a nucleotide sequence of a cDNA encoding a 24p3 (SEQ ID NO:3).

FIG. 3B depicts the predicted amino acid sequence of a 24p3 (SEQ ID NO:4).

FIG. 4 depicts a nucleotide sequence of a cDNA encoding a murine maspin (SEQ ID NO:5).

FIGS. 5A–5B depict a nucleotide sequence of a cDNA encoding a human maspin (SEQ ID NO:6).

FIG. 6 presents expression data for Semaphorin D, Maspin, B94, mel-14 antigen, 24p3, and proliferin.

Like reference symbols in the various drawings indicate like elements.

DETAILED DESCRIPTION

The association between expression of a "resistance sequence" and drug resistance was discovered during an analysis of genes whose expression is altered in a drug resistant EMT-6 tumor compared to an EMT-6 tumor that is not drug resistant. The resistance sequences are semaphorin D, B94, mel-14 antigen, 24p3, proliferin, and maspin. The resistance sequences of the invention include two types of sequences: "up-regulated" sequences (in EMT-6 drug-resistant cells these are semaphorin D, B94, mel-14 antigen, 24p3, and proliferin) and "down-regulated" sequences (in EMT-6 drug-resistant cells, this includes maspin).

Various aspects of the invention are described in further detail in the following subsections.

I. Isolated Nucleic Acid Molecules

One aspect of the invention pertains to isolated nucleic acid molecules that encode resistance proteins or biologically active portions thereof, as well as nucleic acid molecules sufficient for use as hybridization probes to identify resistance protein-encoding nucleic acids (e.g., semaphorin D mRNA, B94 mRNA, mel-14 antigen mRNA, 24p3 mRNA, proliferin mRNA, and maspin mRNA) and fragments for use as PCR primers for the amplification or mutation of resistance nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. Preferably, an "isolated" nucleic acid is free of sequences (preferably protein encoding sequences) which naturally flank the nucleic acid (i.e., sequences located at the 5' and 3' ends of the nucleic acid) in the genomic DNA of the organism from which the nucleic acid is derived. For example, in various embodiments, an isolated resistance nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of use in the present invention, e.g., a nucleic acid molecule having the nucleotide sequence of SEQ ID NO:1, SEQ ID NO:2, SEQ ID NO:3, SEQ ID NO:5, SEQ ID NO:6, a nucleotide sequence depicted in Genbank Accession no.: X85993, L26081, L24118, M92357, M25324, M25280, W13166, X81627, K03235, U54705, or U04313, or a complement of any of these nucleotide sequences, can be isolated using standard molecular biology techniques and the sequence information provided herein. Using all or portion of the nucleic acid sequences of SEQ ID NO:1, SEQ ID NO:2, SEQ ID NO:3, SEQ ID NO:5, SEQ ID NO:6, a nucleotide sequence depicted in Genbank Accession no.: X85993, L26081, L24118, M92357, M25324, M25280, W13166, X81627, K03235, U54705, or U04313, or a complement of any of these nucleotide sequences, as a hybridization probe, resistance nucleic acid molecules can be isolated using standard hybridization and cloning techniques (e.g., as described in Sambrook et al., eds., *Molecular Cloning: A Laboratory Manual.* 2nd, ed., Cold Spring Harbor Laboratory, Cold Spring Harbor Laboratory Press, Cold Spring Harbor, N.Y., 1989).

A nucleic acid of the invention can be amplified using cDNA, mRNA or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to resistance nucleotide sequences can be prepared by standard synthetic techniques, e.g., using an automated DNA synthesizer.

Also useful in the invention are nucleic acid molecules which include only a portion of a nucleic acid sequence encoding a resistance protein, for example, a fragment which can be used as a probe or primer or a fragment encoding a biologically active portion of a resistance protein. The nucleotide sequence of a gene encoding a resistance protein (i.e., a resistance gene) allows for the generation of probes and primers designed for use in identifying and/or cloning resistance homologues in other cell types, e.g., from other tissues, as well as resistance nucleic acid homologues and orthologs from other mammals. The probe/primer typically comprises substantially purified oligonucleotide. The oligonucleotide typically comprises a region of nucleotide sequence that hybridizes under stringent conditions to at least about 12, preferably about 25, more preferably about 50, 75, 100, 125, 150, 175, 200, 250, 300, 350 or 400 consecutive nucleotides of the sense or anti-sense sequence of SEQ ID NO:1, SEQ ID NO:2, SEQ ID NO:3, SEQ ID NO:5, SEQ ID NO:6, a nucleotide sequence depicted in Genbank Accession no.: X85993, L26081, L24118, M92357, M25324, M25280, W13166, X81627, K03235, U54705, or U04313, or of a naturally occurring mutation of SEQ ID NO:1, SEQ ID NO:2, SEQ ID NO:3, SEQ ID NO:5, SEQ ID NO:6, a nucleotide sequence depicted in Genbank Accession no.: X85993, L26081, L24118, M92357, M25324, M25280, W13166, X81627, K03235, U54705, or U04313.

Probes based on a resistance nucleotide sequence can be used to detect transcripts or genomic sequences encoding the same or identical proteins. The probe comprises a labeled group attached thereto, e.g., a radioisotope, a fluorescent compound, an enzyme, or an enzyme co-factor. Such probes can be used as a part of a diagnostic test kit for identifying allelic variants and orthologs of the resistance protein of the present invention, identifying cells or tissue which misexpress a resistance sequence, such as by measuring a level of a resistance protein-encoding nucleic acid in a sample of cells from a subject, e.g., detecting resistance mRNA levels or determining whether a genomic resistance gene has been mutated or deleted.

A nucleic acid fragment encoding a biologically active portion of a resistance protein can be prepared by isolating a portion of SEQ ID NO:1, SEQ ID NO:2, SEQ ID NO:3, SEQ ID NO:5, SEQ ID NO:6, a nucleotide sequence depicted in Genbank Accession no.: X85993, L26081, L24118, M92357, M25324, M25280, W13166, X81627, K03235, U54705, or U04313, which encodes a polypeptide having the biological activity of a resistance protein, expressing the encoded portion of a resistance protein (e.g., by recombinant expression in vitro) and assessing the activity of the encoded portion of the resistance protein.

Other useful nucleic acid molecules include molecules whose nucleotide sequence differs from that of the nucleotide sequence of SEQ ID NO:1, SEQ ID NO:2, SEQ ID NO:3, SEQ ID NO:5, SEQ ID NO:6, a nucleotide sequence depicted in Genbank Accession no.: X85993, L26081, L24118, M92357, M25324, M25280, W13166, X81627, K03235, U54705, and U04313, due to degeneracy of the genetic code and thus encode the same resistance protein as that encoded by the nucleotide sequence shown in SEQ ID NO:1, SEQ ID NO:2, SEQ ID NO:3, SEQ ID NO:5, SEQ ID NO:6, or a nucleotide sequence depicted in Genbank Accession no.: X85993, L26081, L24118, M92357, M25324, M25280, W13166, X81627, K03235, U54705, or U04313.

In addition to the resistance nucleotide sequences shown in SEQ ID NO:1, SEQ ID NO:2, SEQ ID NO:3, SEQ ID NO:5, SEQ ID NO:6, or a nucleotide sequence depicted in Genbank Accession no.: X85993, L26081, L24118, M92357, M25324, M25280, W13166, X81627, K03235, U54705, or U04313, it will be appreciated by those skilled in the art that DNA sequence polymorphisms that lead to changes in the amino acid sequences of a resistance protein may exist within a population (e.g., the human population). Such genetic polymorphism in a resistance gene may exist among individuals within a population due to natural allelic variation. As used herein, the terms "gene" and "recombinant gene" refer to nucleic acid molecules comprising an open reading frame encoding a resistance protein, preferably a mammalian resistance protein. Such natural allelic variations can typically result in 1–5% variance in the nucleotide sequence of the resistance gene. Any and all such nucleotide variations and resulting amino acid polymorphisms in a resistance protein that are the result of natural allelic variation and that do not alter the functional activity of the resistance protein are intended to be within the scope of the invention.

Moreover, nucleic acid molecules encoding resistance proteins from other species (resistance protein orthologs/homologues), which have a nucleotide sequence which differs from that of SEQ ID NO:1, SEQ ID NO:2, SEQ ID NO:3, SEQ ID NO:5, SEQ ID NO:6, or a nucleotide sequence depicted in Genbank Accession no.: X85993, L26081, L24118, M92357, M25324, M25280, W13166, X81627, K03235, U54705, or U04313, may be useful. Nucleic acid molecules corresponding to natural allelic variants and homologues of a resistance cDNA can be isolated based on their identity to a resistance nucleic acid disclosed herein using the a known resistance cDNA, or a portion thereof, as a hybridization probe according to standard hybridization techniques under stringent hybridization conditions. In general, an allelic variant of a gene will be readily identifiable as mapping to the same chromosomal location as said gene.

Other useful nucleic acid molecules include molecules which hybridize under highly stringent conditions or moderately stringent conditions to a selected nucleic acid molecule, e.g., a nucleic acid molecule having the nucleotide sequence of SEQ ID NO:1, SEQ ID NO:2, SEQ ID NO:3, SEQ ID NO:5, SEQ ID NO:6, or a nucleotide sequence depicted in Genbank Accession no.: X85993, L26081, L24118, M92357, M25324, M25280, W13166, X81627, K03235, U54705, or U04313. As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in *Current Protocols in Molecular Biology*, John Wiley & Sons, N.Y. (1989), 6.3.1–6.3.6. A non-limiting example of stringent hybridization conditions are hybridization in 6× sodium chloride/sodium citrate (SSC) at about 45° C., followed by one or more washes in 0.2×SSC, 0.1% SDS at 50–65° C. Preferably, an isolated nucleic acid molecule used in the invention that hybridizes under stringent conditions to the sequence of SEQ ID NO:1, SEQ ID NO:2, SEQ ID NO:3, SEQ ID NO:5, SEQ ID NO:6, or a nucleotide sequence depicted in Genbank Accession no.: X85993, L26081, L24118, M92357, M25324, M25280, W13166, X81627, K03235, U54705, or U04313, corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of a resistance nucleic acid sequence that may exist in the population, the skilled artisan will further appreciate that changes can be introduced by mutation into the nucleotide sequence of SEQ ID NO:1, SEQ ID NO:2, SEQ ID NO:3, SEQ ID NO:5, SEQ ID NO:6, or a nucleotide sequence depicted in Genbank Accession no.: X85993, L26081, L24118, M92357, M25324, M25280, W13166, X81627, K03235, U54705, or U04313, thereby leading to changes in the amino acid sequence of the encoded resistance protein without altering the functional ability of the protein. For example, one can make nucleotide substitutions leading to amino acid substitutions at "non-essential" amino acid residues. A "non-essential" amino acid residue is a residue that can be altered from the wild-type sequence (e.g., the sequence of SEQ ID NO:4, or an amino acid sequence depicted in Genbank Accession no.: X85993, L26081, L24118, M92357, M25324, M25280, W13166, X81627, K03235, U54705, or U04313) without altering the biological activity, whereas an "essential" amino acid residue is required for biological activity. For example, amino acid residues that are conserved among the resistance proteins of various species are predicted to be particularly unamenable to alteration.

Other useful nucleic acid molecules include nucleic acid molecules encoding resistance proteins that contain changes in amino acid residues that are not essential for activity. Such resistance proteins differ in amino acid sequence from SEQ ID NO:4 or an amino acid sequence depicted in Genbank Accession no.: X85993, L26081, L24118, M92357, M25324, M25280, W13166, X81627, K03235, U54705, or U04313, and yet retain biological activity. Such an isolated nucleic acid molecule can include a nucleotide sequence encoding a protein that includes an amino acid sequence that is at least about 45% identical, 65%, 75%, 85%, 95%, or 98% identical to the amino acid sequence of SEQ ID NO:4, or an amino acid sequence depicted in Genbank Accession no.: X85993, L26081, L24118, M92357, M25324, M25280, W13166, X81627, K03235, U54705, or U04313.

An isolated nucleic acid molecule encoding a resistance polypeptide can be created by introducing one or more nucleotide substitutions, additions or deletions into the nucleotide sequence of a resistance nucleic acid (SEQ ID NO:1, SEQ ID NO:2, SEQ ID NO:3, SEQ ID NO:5, SEQ ID NO:6, or a nucleic acid sequence depicted in Genbank Accession no.: X85993, L26081, L24118, M92357, M25324, M25280, W13166, X81627, K03235, U54705, or U04313) such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a resistance polypeptide is preferably replaced with another amino acid residue from the same side chain family. Alternatively, mutations can be introduced randomly along all or part of a resistance coding sequence, such as by saturation mutagenesis, and the resultant mutants can be screened for biological activity specific to that resistance protein to identify mutants that retain activity. Following mutagenesis, the encoded protein can be expressed recombinantly and the activity of the protein can be determined.

Also useful are antisense nucleic acid molecules, i.e., molecules which are complementary to a sense nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire coding strand of a gene encoding a resistance protein, or to only a portion thereof, e.g., all or part of the protein coding region (or open reading frame). An antisense nucleic acid molecule can be antisense to a noncoding region of the coding strand of a nucleotide sequence encoding a resistance protein. The noncoding regions ("5' and 3' untranslated regions") are the 5' and 3' sequences which flank the coding region and are not translated into amino acids.

Given the coding strand sequences encoding a resistance protein, antisense nucleic acids of the invention can be designed according to the rules of Watson and Crick base pairing. The antisense nucleic acid molecule can be complementary to the entire coding region of a resistance mRNA, but more preferably is an oligonucleotide which is antisense to only a portion of the coding or noncoding region of the mRNA. For example, the antisense oligonucleotide can be complementary to the region surrounding the translation start site of the mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

A useful antisense nucleic acid molecule is typically administered to a subject or generated in situ such that they hybridize with or bind to cellular mRNA and/or genomic DNA encoding a resistance protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

A useful antisense nucleic acid molecule can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) Nucleic Acids. Res. 15:6625–6641). The antisense nucleic acid molecule can also comprise a 2'-o-methylribonucleotide (Inoue et al. (1987) Nucleic Acids Res. 15:6131–6148) or a chimeric RNA-DNA analogue (Inoue et al. (1987) FEBS Lett. 215:327–330).

Other useful molecules include ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) Nature 334:585–591)) can be used to catalytically cleave resistance mRNA transcripts to thereby inhibit translation of resistance mRNA. A ribozyme having specificity for a resistance protein-encoding nucleic acid can be designed based upon the nucleotide sequence of a cDNA of one of the resistance genes described herein. For example, a derivative of a Tetrahymena L-19 IVS RNA can be constructed in which the nucleotide sequence of the active site is complementary to the nucleotide sequence to be cleaved in a resistance protein-encoding mRNA. See, e.g., Cech et al. U.S. Pat. No. 4,987,071; and Cech et al. U.S. Pat. No. 5,116,742. Alternatively, a resistance mRNA can be used to select a catalytic RNA having a specific ribonuclease activity from a pool of RNA molecules. See, e.g., Bartel and Szostak (1993) Science 261:1411–1418.

Also useful are nucleic acid molecules which form triple helical structures. For example, expression of a resistance gene can be inhibited by targeting nucleotide sequences complementary to the regulatory region of the resistance gene (e.g., a resistance gene promoter and/or enhancer(s)) to form triple helical structures that prevent transcription of the resistance gene in target cells. See generally, Helene (1991) Anticancer Drug Des. 6(6):569–84; Helene (1992) Ann. N.Y. Acad. Sci. 660:27–36; and Maher (1992) Bioassays 14(12):807–15.

Useful nucleic acid molecules can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) Bioorganic & Medicinal Chemistry 4(1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) supra; Perry-O'Keefe et al. (1996) Proc. Natl. Acad. Sci. USA 93: 14670–675.

PNAs can be used for therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996) supra; or as probes or primers for DNA sequence and hybridization (Hyrup (1996) supra; Perry-O'Keefe et al. (1996) Proc. Natl. Acad. Sci. USA 93: 14670–675).

PNAs of a resistance sequence can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of a resistance sequence can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996) supra). The synthesis of PNA-DNA chimeras can be performed as described in Hyrup (1996) supra and Finn et al. (1996) Nucleic Acids Research 24(17):3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag et al. (1989) Nucleic Acid Res. 17:5973–88). PNA monomers are then coupled in a stepwise manner to produce a chimeric molecule with a 5' PNA segment and a 3' DNA segment (Finn et al. (1996) Nucleic Acids Research 24(17):3357–63). Alternatively, chimeric molecules can be synthesized with a 5' DNA segment and a 3' PNA segment (Peterser et al. (1975) Bioorganic Med. Chem. Lett. 5:1119–11124).

A useful oligonucleotide may include other appended groups such as peptides (e.g., for targeting host cell receptors in vivo), or agents facilitating transport across the cell membrane (see, e.g., Letsinger et al. (1989) Proc. Natl. Acad. Sci. USA 86:6553–6556; Lemaitre et al. (1987) Proc. Natl. Acad. Sci. USA 84:648–652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al. (1988) Bio/Techniques 6:958–976) or intercalating agents (see, e.g., Zon (1988) Pharm. Res. 5:539–549). To this end, the oligonucleotide may be conjugated to another molecule, e.g., a peptide, hybridization triggered cross-linking agent, transport agent, hybridization-triggered cleavage agent, etc.

II. Isolated Resistance Proteins and Anti-Resistance Protein Antibodies

Useful molecules include an isolated resistance protein, and biologically active portions thereof, as well as polypeptide fragments suitable for use as immunogens to raise anti-resistance protein antibodies. A native resistance protein can be isolated from cells or tissue sources by an appropriate purification scheme using standard protein purification techniques. A resistance protein may be produced by recombinant DNA techniques. Alternative to recombinant expression, a resistance protein or polypeptide can be synthesized chemically using standard peptide synthesis techniques. Such resistance proteins and polypeptides can possess at least one biological activity possessed by a naturally occurring human resistance protein. The biological activity will depend on the specific resistance protein or polypeptide, although, in general all will have the ability to increase drug resistance in certain tumor or cancer cell lines. Examples of other activities include, e.g., for semaphorin D, the ability to act as an axonal guidance signal; for B94, a role in pro-inflammatory response and hematopoetic development; for mel-14 antigen, the ability to mediate adherence of lymphocytes to endothelial cells; for 24p3, ability to bind small hydrophobic molecules; for proliferin, induction of endothelial cell chemotaxis through a G protein-coupled, mitogen-activated protein kinase-dependent pathway; and for maspin, the ability to act as a protease inhibitor, or binding and inhibiting single-chain tissue plasminogen activator.

An "isolated" or "purified" protein or biologically active portion thereof is substantially free of cellular material or other contaminating proteins from the cell or tissue source from which the resistance protein is derived, or substantially free from chemical precursors or other chemicals when chemically synthesized. The language "substantially free of cellular material" includes preparations of a resistance protein in which the protein is separated from cellular components of the cells from which it is isolated or recombinantly produced. Thus, a resistance protein that is substantially free of cellular material includes preparations of a resistance protein having less than about 30%, 20%, 10%, or 5% (by dry weight) of proteins other than the resistance protein (also referred to herein as a "contaminating protein"). When the resistance protein or biologically active portion thereof is recombinantly produced, it is also preferably substantially free of culture medium, i.e., culture medium represents less than about 20%, 10%, or 5% of the volume of the protein preparation. When a resistance protein is produced by chemical synthesis, it is preferably substantially free of chemical precursors or other chemicals, i.e., it is separated from chemical precursors or other chemicals which are involved in the synthesis of the protein.

Accordingly such preparations of a resistance protein have less than about 30%, 20%, 10%, 5% (by dry weight) of chemical precursors or chemicals other than the resistance protein.

Biologically active portions of a resistance protein include peptides comprising amino acid sequences sufficiently identical to or derived from the amino acid sequence of the resistance protein (e.g., the amino acid sequence of SEQ ID NO:4, or an amino acid sequence depicted in Genbank Accession no.: X85993, L26081, L24118, M92357, M25324, M25280, W13166, X81627, K03235, U54705, or U04313), which include fewer amino acids than the full-length resistance protein, and exhibit at least one activity of the resistance protein. Typically, biologically active portions comprise a domain or motif with at least one activity of the resistance protein. A biologically active portion of a resistance protein can be a polypeptide which is, for example, 10, 25, 50, 100 or more amino acids in length. Preferred biologically active polypeptides include one or more identified structural domains of the resistance protein.

Moreover, other biologically active portions, in which other regions of the protein are deleted, can be prepared by recombinant techniques and evaluated for one or more of the functional activities of a native resistance protein.

A resistance protein has the amino acid sequence of semaphorin D, B94, mel-14 antigen, 24p3, proliferin, or maspin. Other useful resistance proteins are substantially identical to SEQ ID NO:4, or an amino acid sequence depicted in Genbank Accession no.: X85993, L26081, L24118, M92357, M25324, M25280, W13166, X81627, K03235, U54705, or U04313, and retain the functional activity of the protein of SEQ ID NO:4, or an amino acid sequence depicted in Genbank Accession no.: X85993, L26081, L24118, M92357, M25324, M25280, W13166, X81627, K03235, U54705, or U04313, yet differ in amino acid sequence due to natural allelic variation or mutagenesis. A useful resistance protein is a protein which includes an amino acid sequence at least about 80%, preferably 82%, 85%, 95%, 98%, or 99% identical to the amino acid sequence of SEQ ID NO:4, or an amino acid sequence depicted in Genbank Accession no.: X85993, L26081, L24118, M92357, M25324, M25280, W13166, X81627, K03235, U54705, or U04313, and retains the functional activity of the resistance protein, e.g., that depicted in SEQ ID NO:4, or an amino acid sequence depicted in Genbank Accession no.: X85993, L26081, L24118, M92357, M25324, M25280, W13166, X81627, K03235, U54705, or U04313.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions× 100).

The determination of percent homology between two sequences can be accomplished using a mathematical algorithm. A preferred, non-limiting example of a mathematical algorithm utilized for the comparison of two sequences is the algorithm of Karlin and Altschul (1990) Proc. Nat'l Acad. Sci. USA 87:2264–2268, modified as in Karlin and Altschul (1993) Proc. Nat'l Acad. Sci. USA 90:5873–5877. Such an algorithm is incorporated into the NBLAST and XBLAST programs of Altschul, et al. (1990) J. Mol. Biol. 215:403–410. BLAST nucleotide searches can be performed with the NBLAST program, score=100, wordlength=12 to obtain nucleotide sequences similar or homologous to resistance nucleic acid molecules of the invention. BLAST protein searches can be performed with the XBLAST program, score=50, wordlength=3 to obtain amino acid sequences homologous to a resistance protein molecule. To obtain gapped alignments for comparison purposes, Gapped BLAST can be utilized as described in Altschul et al., (1997) Nucleic Acids Res. 25:3389–3402. When utilizing BLAST and Gapped BLAST programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, only exact matches are counted.

The invention also provides resistance protein chimeric or fusion proteins. As used herein, a resistance "chimeric protein" or "fusion protein" comprises a resistance polypeptide operatively linked to a non-resistance protein polypeptide. A "resistance polypeptide" refers to a polypeptide having an amino acid sequence corresponding to a resistance protein (e.g., semaphorin D, B94, mel-14 antigen, 24p3, proliferin, or maspin), whereas a "non-resistance polypeptide" refers to a polypeptide having an amino acid sequence corresponding to a protein which is not substantially identical to a resistance protein, e.g., a protein which is different from the resistance proteins of interest and which is derived from the same or a different organism. Within a resistance fusion protein, the resistance polypeptide can correspond to all or a portion of a resistance protein, preferably at least one biologically active portion of a resistance protein. Within the fusion protein, the term "operatively linked" is intended to indicate that the resistance polypeptide and the non-resistance polypeptide are fused in-frame to each other. The non-resistance polypeptide can be fused to the N-terminus or C-terminus of the resistance polypeptide.

One useful fusion protein is a GST-resistance fusion protein in which a resistance sequence is fused to the C-terminus of the GST sequence. Such fusion proteins can facilitate the purification of a recombinant resistance protein.

Another useful molecule is a fusion protein containing a signal sequence from another protein. In certain host cells (e.g., mammalian host cells), expression and/or secretion of a resistance protein can be increased through use of a heterologous signal sequence. For example, the gp67 secretory sequence of the baculovirus envelope protein can be used as a beterologous signal sequence (Current Protocols in Molecular Biology, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Molecular Cloning, Sambrook et al, second edition, Cold Spring Harbor laboratory press, 1989) and the protein A secretory signal (Pharmacia Biotech; Piscataway, N.J.).

A useful fusion protein can be a resistance protein-immunoglobulin fusion protein in which all or part of the resistance protein is fused to sequences derived from a member of the immunoglobulin protein family. The resistance protein-immunoglobulin fusion proteins of the invention can be incorporated into pharmaceutical compositions and administered to a subject to inhibit an interaction between a resistance protein ligand and the resistance protein. Inhibition of the resistance protein ligand/resistance protein interaction may be useful therapeutically for both the treatment of proliferative and differentiative disorders. Moreover, the resistance-immunoglobulin fusion proteins of the invention can be used as immunogens to produce anti-resistance protein antibodies in a subject, to purify resistance protein ligands and in screening assays to identify molecules which inhibit the interaction of a resistance protein with a its ligand.

A resistance protein chimeric or fusion protein can be produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. Alternatively, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., Current Protocols in Molecular Biology, Ausubel et al. eds., John Wiley & Sons: 1992). Moreover, many expression vectors are commercially available that already encode a fusion moiety (e.g., a GST polypeptide). A resistance protein-encoding nucleic acid can be cloned into such an expression vector such that the fusion moiety is linked in-frame to the sequence encoding the resistance protein.

Variants of a resistance protein which function as either an agonist of a resistance protein (mimetics) or as an antagonist of a resistance protein are useful. Variants of the resistance protein can be generated by mutagenesis, e.g., discrete point mutation or truncation of the resistance protein. An agonist of a resistance protein can retain substantially the same, or a subset, of the biological activities of the naturally occurring form of the resistance protein. An antagonist of a resistance protein can inhibit one or more of the activities of the naturally occurring form of a resistance protein. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the resistance protein.

Variants of a resistance protein which function as either agonists of the resistance protein (mimetics) or as antagonists of the resistance protein can be identified by screening combinatorial libraries of mutants, e.g., truncation mutants, of the resistance protein for resistance protein agonist or antagonist activity. A library of resistance protein variants can be produced by, for example, enzymatically ligating a mixture of synthetic oligonucleotides into gene sequences such that a degenerate set of potential resistance protein encoding sequences is expressible as individual polypeptides, or alternatively, as a set of larger fusion proteins (e.g., for phage display) containing the set of resistance protein sequences therein. There are a variety of methods which can be used to produce libraries of potential resistance protein variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential resistance protein sequences. Methods for synthesizing degenerate oligonucleotides are known in the art (see, e.g., Narang (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of a resistance protein coding sequence can be used to generate a variegated population of resistance protein fragments for screening and subsequent selection of variants of the resistance protein. For example, a library of coding sequence fragments can be generated by treating a double stranded PCR fragment of a resistance protein coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of a resistance protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of a resistance protein. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a resistance protein (Arkin and Yourvan (1992) *Proc. Natl. Acad. Sci. USA* 89:7811–7815; Delgrave et al. (1993) *Protein Engineering* 6(3):327–331).

An isolated resistance protein, or a portion or fragment thereof, can be used as an immunogen to generate antibodies that bind the resistance protein using standard techniques for polyclonal and monoclonal antibody preparation. The full-length resistance protein can be used or, alternatively, the invention provides antigenic peptide fragments of the resistance protein for use as immunogens. The antigenic peptide of a resistance protein comprises at least 8 (preferably 10, 15, 20, or 30) amino acid residues of the amino acid sequence shown in SEQ ID NO:4, or an amino acid sequence depicted in Genbank Accession no.: X85993, L26081, L24118, M92357, M25324, M25280, W13166, X81627, K03235, U54705, or U04313, and encompasses an epitope of the resistance protein such that an antibody raised against the peptide forms a specific immune complex with the resistance protein.

Preferred epitopes encompassed by the antigenic peptide are regions of a resistance protein that are located on the surface of the protein, e.g., hydrophilic regions.

A resistance protein immunogen typically is used to prepare antibodies by immunizing a suitable subject, (e.g., rabbit, goat, mouse or other mammal) with the immunogen. An appropriate immunogenic preparation can contain, for example, a recombinantly expressed resistance protein or a chemically synthesized resistance polypeptide. The preparation can further include an adjuvant, such as Freund's complete or incomplete adjuvant, or similar immunostimulatory agent. Immunization of a suitable subject with an immunogenic resistance protein preparation induces a polyclonal antibody response against that resistance protein.

Anti-resistance protein antibodies are useful in the methods of the invention. The term antibody refers to immunoglobulin molecules and immunologically active portions of immunoglobulin molecules, i.e., molecules that contain an antigen binding site which specifically binds an antigen, such as a resistance protein. A molecule which specifically binds to a resistance protein is a molecule which binds the resistance protein, but does not substantially bind other molecules in a sample, e.g., a biological sample, which naturally contains the resistance protein. Examples of immunologically active portions of immunoglobulin molecules include F(ab) and F(ab')$_2$ fragments which can be generated by treating the antibody with an enzyme such as pepsin. The term monoclonal antibody or monoclonal antibody composition refers to a population of antibody molecules that contain only one species of an antigen binding site capable of immunoreacting with a particular epitope of the resistance protein. A monoclonal antibody composition thus typically displays a single binding affinity for a particular resistance protein with which it immunoreacts.

Polyclonal anti-resistance protein antibodies can be prepared as described above by immunizing a suitable subject with a specific resistance protein immunogen. The anti-resistance protein antibody titer in the immunized subject can be monitored over time by standard techniques, such as with an enzyme linked immunosorbent assay (ELISA) using immobilized resistance protein. If desired, the antibody molecules directed against a particular resistance protein can be isolated from the mammal (e.g., from the blood) and further purified by well-known techniques, such as protein A chromatography to obtain the IgG fraction. At an appropriate time after immunization, e.g., when the anti-resistance protein antibody titers are highest, antibody-producing cells can be obtained from the subject and used to prepare monoclonal antibodies by standard techniques, such as the hybridoma technique originally described by Kohler and Milstein (1975) *Nature* 256:495–497, the human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing various antibodies monoclonal antibody hybridomas is well known (see generally Current Protocols in Immunology (1994) Coligan et al. (eds.) John Wiley & Sons, Inc., New York, N.Y.). Briefly, an immortal cell line (typically a myeloma) is fused to lymphocytes (typically splenocytes) from a mammal immunized with a resistance protein immunogen as described above, and the culture supernatants of the resulting hybridoma cells are screened to identify a hybridoma producing a monoclonal antibody that binds the resistance protein.

Any of the many well known protocols used for fusing lymphocytes and immortalized cell lines can be applied for the purpose of generating an anti-resistance protein monoclonal antibody (see, e.g., Current Protocols in Immunology, supra; Galfre et al. (1977) *Nature* 266:55052; R. H. Kenneth, in *Monoclonal Antibodies: A New Dimension In Biological Analyses*, Plenum Publishing Corp., New York, N.Y. (1980); and Lerner (1981) *Yale J. Biol. Med.*, 54:387–402. Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line, e.g., a myeloma cell line that is sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind the resistance protein of interest, e.g., using a standard ELISA assay.

Alternative to preparing monoclonal antibody-secreting hybridomas, a monoclonal anti-resistance protein antibody can be identified and isolated by screening a recombinant combinatorial immunoglobulin library (e.g., an antibody phage display library) with the resistance protein of interest to thereby isolate immunoglobulin library members that bind the resistance protein. Kits for generating and screening phage display libraries are commercially available (e.g., the Pharmacia *Recombinant Phage Antibody System*, Catalog No. 27-9400-01; and the Stratagene *SurfZAP Phage Display Kit*, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication WO 92/20791; PCT Publication No. WO 92/15679; PCT Publication WO 93/01288; PCT Publication No. WO 92/01047; PCT Publication No. WO 92/09690; PCT Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J* 12:725–734.

Additionally, recombinant antibodies that recognize a specific resistance protein, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041–1043; Liu et al. (1987) *Proc. Natl. Acad. Sci. USA* 84:3439–3443; Liu et al. (1987) *J Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, (1985) *Science* 229:1202–1207; Oi et al. (1986) *Bio/Techniques* 4:214; U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

An anti-resistance protein antibody (e.g., monoclonal antibody) can be used to isolate a resistance protein by standard techniques, such as affinity chromatography or immunoprecipitation. An anti-resistance protein antibody can facilitate the purification of natural resistance protein from cells and of recombinantly produced resistance protein expressed in host cells. Moreover, an anti-resistance protein antibody can be used to detect a resistance protein (e.g., in a cellular lysate or cell supernatant) in order to evaluate the abundance and pattern of expression of the resistance protein. Anti-resistance protein antibodies can be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, b-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

III. Recombinant Expression Vectors and Host Cells

Vectors, particularly expression vectors, containing a nucleic acid encoding a resistance protein (or a portion thereof) are useful. A vector is a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operatively linked. In general, expression vectors of utility in recombinant DNA techniques are often in the form of plasmids (vectors, e.g., viral vectors, replication defective retroviruses, adenoviruses and adeno-associated viruses).

Useful recombinant expression vectors comprise a resistance nucleic acid in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. An expression vector can be introduced into host cells to thereby produce proteins or peptides, including fusion proteins or peptides, encoded by nucleic acids as described herein (e.g., resistance proteins, mutant forms of a resistance protein, fusion proteins, etc.).

The recombinant expression vectors can be designed for expression of a resistance protein in prokaryotic or eukaryotic cells, e.g., bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11 d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111–2118). Such alteration of nucleic acid sequences of the invention can be carried out by standard DNA synthesis techniques.

A resistance protein expression vector is a yeast expression vector. Examples of vectors for expression in yen be a *S. cerivisae* include pYepSec1 (Baldari et al. (1987) *EMBO J.* 6:229–234), pMFa (Kurjan and Herskowitz, (1982) *Cell* 30:933–943), pJRY88 (Schultz et al. (1987) *Gene* 54:113–123), pYES2 (Invitrogen Corporation, San Diego, Calif.), and picZ (InVitrogen Corp, San Diego, Calif.).

Alternatively, a resistance protein can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

A resistance nucleic acid can be expressed in mammalian cells using a mammalian expression vector. Examples of mammalian expression vectors include pCDM8 (Seed (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al. (supra).

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Baneiji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873, 316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

Other useful recombinant expression vectors are those comprising an resistance nucleic acid molecule cloned into the expression vector in an antisense orientation. That is, the DNA molecule is operatively linked to a regulatory sequence in a manner which allows for expression (by transcription of the DNA molecule) of an RNA molecule which is antisense to resistance mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes See Weintraub et al., *Reviews—Trends in Genetics*, Vol. 1(1) 1986.

Host cells into which a resistance expression vector has been introduced are useful in certain methods of the invention. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a resistance protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a resistance protein or can be introduced on a separate vector. Cells stably transfected with the introduced nucleic acid can be identified by drug selection (e.g., cells that have incorporated the selectable marker gene will survive, while the other cells die).

A prokaryotic or eukaryotic host cell in culture can be used to produce (i.e., express) a resistance protein, e.g., by culturing the host cell (into which a recombinant expression vector encoding a resistance protein has been introduced) in a suitable medium such that the resistance protein is produced. The resistance protein can then be isolated from the medium or the host cell.

IV. Pharmaceutical Compositions

Resistance proteins, and anti-resistance protein antibodies, and modulators of expression or activity (also referred to herein as "active compounds") of a resistance sequence can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Resistance nucleic acid molecules useful in the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The resistance nucleic acid molecules, proteins, protein homologues, and antibodies described herein can be used in screening assays, predictive medicine (e.g., diagnostic assays, prognostic assays, monitoring clinical trials, and pharmacogenomics), and methods of treatment (e.g., therapeutic treatment methods and prophylactic treatment methods).

A. Screening Assays

The invention provides a method (also referred to herein as a "screening assay") for identifying modulators, i.e., candidate or test compounds or agents (e.g., peptides, peptidomimetics, small molecules or other drugs) which bind to a resistance protein or have a stimulatory or inhibitory effect on, for example, expression or activity of a resistance sequence. Such identified compounds may be useful for the modulation of drug resistance.

In one embodiment, the invention provides assays for screening candidate or test compounds which bind to or modulate the activity of a resistance protein or polypeptide or biologically active portion thereof. The test compounds of the present invention can be obtained using any of the numerous approaches in combinatorial library methods known in the art, including: biological libraries; natural products libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other approaches are applicable to peptide, non-peptide oligomer or small molecule libraries of compounds (Lam, (1997) Anticancer Drug Des. 12:145).

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233.

Libraries of compounds may be presented in solution (e.g., Houghten (1992) Bio/Techniques 13:412–421), or on beads (Lam (1991) Nature 354:82–84), chips (Fodor (1993) Nature 364:555–556), bacteria (U.S. Pat. No. 5,223,409), spores (U.S. Pat. Nos. 5,571,698; 5,403,484; and 5,223, 409), plasmids (Cull et al. (1992) Proc. Natl. Acad. Sci. USA 89:1865–1869) or on phage (Scott and Smith (1990) Science 249:386–390; Devlin (1990) Science 249:404–406; Cwirla et al. (1990) Proc. Natl. Acad. Sci. 87:6378–6382; and Felici (1991) J. Mol. Biol. 222:301–310).

In one embodiment, an assay is a cell-based assay in which a cell which expresses a resistance protein, or a biologically active portion thereof, is contacted with a test compound and the ability of the test compound to bind to the resistance protein determined. The cell, for example, can be a yeast cell or a cell of mammalian origin. Determining the ability of the test compound to bind to the resistance protein can be accomplished, for example, by coupling the test compound with a radioisotope or enzymatic label such that binding of the test compound to the resistance protein or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In a preferred embodiment, the assay comprises contacting a cell which expresses a resistance protein, or a biologically active portion thereof, with a known compound which binds the resistance protein to form an assay mixture, contacting the assay mixture with a test compound, and determining the ability of the test compound to interact with a resistance protein, wherein determining the ability of the test compound to interact with the resistance protein comprises determining the ability of the test compound to preferentially bind to the resistance protein or a biologically active portion thereof as compared to the known compound.

In another embodiment, an assay is a cell-based assay comprising contacting a cell expressing a resistance protein, or a biologically active portion thereof, with a test compound and determining the ability of the test compound to modulate (e.g., stimulate or inhibit) the activity of the resistance protein or biologically active portion thereof. Determining the ability of the test compound to modulate the activity of the resistance protein or a biologically active portion thereof can be accomplished, for example, by determining the ability of the resistance protein to bind to or interact with a target molecule. As used herein, a "target molecule" is a molecule with which a resistance protein binds or interacts in nature, for example, a molecule in the nucleus or cytoplasm of a cell which expresses a resistance protein. A resistance target molecule can be a non-resistance molecule or a resistance protein or polypeptide. The target, for example, can be a second intracellular protein which has catalytic activity, a protein which naturally binds to a resistance protein, or a protein which facilitates the association of DNA with a resistance protein.

Determining the ability of a resistance protein to bind to or interact with a target molecule can be accomplished by one of the methods described above for determining direct binding. In a preferred embodiment, determining the ability of the resistance protein to bind to or interact with a target molecule can be accomplished by determining the activity of the target molecule or detecting a cellular response, for example, cell survival or cell proliferation in the presence of a chemotherapeutic drug.

In yet another embodiment, an assay of the present invention is a cell-free assay comprising contacting a resistance protein or biologically active portion thereof with a test compound and determining the ability of the test compound to bind to the resistance protein or biologically active portion thereof. Binding of the test compound to the resistance protein can be determined either directly or indirectly as described above. In a preferred embodiment, the assay includes contacting the resistance protein or biologically active portion thereof with a known compound which binds the resistance protein to form an assay mixture, contacting the assay mixture with a test compound, and determining the ability of the test compound to interact with a resistance protein, wherein determining the ability of the test compound to interact with the resistance protein comprises determining the ability of the test compound to preferentially bind to the resistance protein or biologically active portion thereof as compared to the known compound.

In another embodiment, an assay is a cell-free assay comprising contacting a resistance protein or biologically active portion thereof with a test compound and determining the ability of the test compound to modulate (e.g., stimulate or inhibit) the activity of the resistance protein or biologically active portion thereof. Determining the ability of the test compound to modulate the activity of the resistance can be accomplished, for example, by determining the ability of the resistance protein to bind to a target molecule by one of the methods described above for determining direct binding. In an alternative embodiment, determining the ability of the test compound to modulate the activity of a resistance protein can be accomplished by determining the ability of the resistance protein further modulate a target molecule. For example, the catalytic/enzymatic activity of the target molecule on an appropriate substrate can be determined as previously described.

In yet another embodiment, the cell-free assay comprises contacting a resistance protein or biologically active portion thereof with a known compound which binds the resistance protein to form an assay mixture, contacting the assay mixture with a test compound, and determining the ability of the test compound to interact with the resistance protein, wherein determining the ability of the test compound to interact with the resistance protein comprises determining the ability of the resistance protein to preferentially bind to or modulate the activity of a resistance target molecule.

The cell-free assays of the present invention are amenable to use of both native and variant forms (e.g., peptide fragments and fusion proteins) of a resistance protein. In the case of cell-free assays comprising a hydrophobic form of a resistance protein, it may be desirable to utilize a solubilizing agent such that the hydrophobic form of the resistance protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton□ X-100, Triton□ X-114, Thesit□, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either a resistance protein or its target molecule to facilitate separation of complexed from uncomplexed forms of one or both of the proteins, as well as to accommodate automation of the assay. Binding of a test compound to a resistance protein, or interaction of a resistance protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, a fusion protein composed of glutathione-S-transferase and a resistance protein polypeptide or glutathione-S-transferase/target fusion proteins can be adsorbed onto glutathione Sepharose beads (Sigma Chemical; St. Louis, Mo.) or glutathione derivatized microtitre plates, which are then combined with the test compound or the test compound and either the non-adsorbed target protein or resistance protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of binding to a resistance protein or activity of a resistance protein determined using standard techniques.

Other techniques for immobilizing proteins on matrices can also be used in the screening assays of the invention. For example, either a resistance protein or its target molecule can be immobilized utilizing conjugation of biotin and streptavidin. Biotinylated resistance protein or target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with a resistance protein or target molecules but which do not interfere with binding of the resistance protein to its target molecule can be derivatized to the wells of the plate, and unbound target or resistance protein trapped in the wells by antibody conjugation. Methods for detecting such complexes, in addition to those described above for the GST-immobilized complexes, include immunodetection of complexes using antibodies reactive with the resistance protein or target molecule, as well as enzyme-linked assays which rely on detecting an enzymatic activity associated with the resistance protein or target molecule.

In another embodiment, modulators of expression of a resistance sequence are identified in a method in which a cell is contacted with a candidate compound and the expression of the resistance sequence in the cell is determined. The level of expression of resistance sequence in the presence of the candidate compound is compared to the level of expression of the resistance sequence in the absence of the candidate compound. The candidate compound can then be identified as a modulator of resistance sequence expression based on this comparison. For example, when expression of a resistance mRNA or resistance protein is greater (statistically significantly greater) in the presence of the candidate compound than in its absence, the candidate compound is identified as a stimulator of the resistance mRNA or resistance protein expression. Alternatively, when expression of a resistance mRNA or resistance protein is less (statistically significantly less) in the presence of the candidate compound than in its absence, the candidate compound is identified as an inhibitor of the resistance mRNA or resistance protein expression. The level of resistance mRNA or resistance protein expression in the cells, or the number of copies of a resistance gene per cell can be determined by methods described herein for detecting resistance genomic DNA, mRNA, or protein.

Resistance proteins can be used as "bait proteins" in a two-hybrid assay or three hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *BioTechniques* 14:920–924; Iwabuchi et al. (1993) *Oncogene* 8:1693–1696; and WO94/10300), to identify other proteins, which bind to or interact with a resistance protein ("resistance protein-binding proteins" or "resistance-bp") and modulate activity of the resistance protein. Such resistance-binding proteins are also likely to be involved in DNA damage repair or cellular resistance to chemotherapeutic drugs.

The two-hybrid system is based on the modular nature of most transcription factors, which consist of separable DNA-binding and activation domains. Briefly, the assay utilizes two different DNA constructs. In one construct, the gene that codes for a resistance protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a resistance protein-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the resistance protein.

This invention further pertains to novel agents identified by the above-described screening assays and uses thereof for treatments as described herein.

B. Predictive Medicine

The present invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the present invention relates to diagnostic assays for determining resistance protein and/or nucleic acid expression as well as activity of a resistance protein, in the context of a biological sample (e.g., blood, serum, cells, tissue) to thereby determine whether an individual is afflicted with a disease or disorder, or is at risk of developing a disorder, associated with aberrant resistance expression or activity (e.g., altered drug resistance). The invention also provides for prognostic (or predictive) assays for determining whether an individual is at risk of developing a disorder associated with a resistance protein, nucleic acid expression or activity (e.g., altered drug resistance). For example, mutations in a resistance gene can be assayed in a biological sample. Such assays can be used for prognostic or predictive purpose to thereby prophylactically treat an individual prior to the onset of a disorder characterized by or associated with a resistance protein, nucleic acid expression or activity. For example, because a specific up-regulated resistance protein is expressed at a higher level in a drug resistant tumor cell line (e.g., semaphorin D in CDDP-resistant EMT6 cells) than non-drug resistant tumor cell lines, higher than normal expression of the up-regulated protein can be used as an indicator of drug resistance. Similarly, because a down-regulated resistance protein (e.g., maspin) is expressed at a lower level in a drug resistant tumor cell line (e.g., in CDDP-resistant EMT6 cells) than non-drug resistant tumor cell lines, lower than normal expression of maspin in this cell type of cell line is indicative of drug resistance.

Another aspect of the invention provides methods for determining a resistance protein, nucleic acid expression or resistance protein activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Yet another aspect of the invention pertains to monitoring the influence of agents (e.g., drugs or other compounds) on the expression or activity of a resistance sequence in clinical trials.

These and other agents are described in further detail in the following sections.

1. Diagnostic Assays

Methods of assessing expression are useful, especially undesirable expression, of a cellular resistance sequence. Undesirable expression (e.g., increased expression of an up-regulated sequence or decreased expression of a down-regulated sequence) may indicate the presence, persistence or reappearance of drug-resistant (e.g., resistant to cisplatin or cyclophosphamide) tumor cells in an individual's tissue. More generally, aberrant expression may indicate the occurrence of a deleterious or disease-associated phenotype contributed to by the expression of a resistance sequence.

An exemplary method for detecting the presence or absence of a resistance sequence in a biological sample involves obtaining a biological sample (preferably from a body site implicated in a possible diagnosis of diseased or malignant tissue) from a test subject and contacting the biological sample with a compound or an agent capable of detecting the resistance sequence (e.g., mRNA, genomic DNA, polypeptide) such that the presence of the resistance sequence is detected in the biological sample. The presence and/or relative abundance (e.g., compared to a normal or non-drug resistant tumor of the same type) of the resistance sequence indicates aberrant or undesirable expression of a cellular resistance gene, and correlates with the occurrence in situ of cells having a drug-resistant phenotype.

A preferred agent for detecting a resistance mRNA or genomic DNA encoding a resistance protein is a labeled nucleic acid probe capable of hybridizing to the resistance mRNA or genomic DNA. The nucleic acid probe can be, for example, a full-length resistance mRNA, such as the nucleic acid of SEQ ID NO:1, SEQ ID NO:2, SEQ ID NO:3, SEQ ID NO:5, SEQ ID NO:6, or a nucleic acid sequence depicted in Genbank Accession no.: X85993, L26081, L24118, M92357, M25324, M25280, W13166, X81627, K03235, U54705, or U04313, or a portion thereof, such as an oligonucleotide of at least 15, 30, 50, 100, 250 or 500 nucleotides in length and sufficient to specifically hybridize under stringent conditions to the resistance mRNA or genomic DNA. Other suitable probes for use in the diagnostic assays of the invention are described herein.

A preferred agent for detecting a resistance protein is an antibody capable of binding to the resistance protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect resistance mRNA, protein, or genomic DNA in a biological sample in vitro as well as in vivo. For example, in vitro techniques for detection of a resistance mRNA include Northern hybridizations and in situ hybridizations. In vitro techniques for detection of a resistance protein include enzyme linked immunosorbent assays (ELISAs), Western blots, immunoprecipitations and immunofluorescence. In vitro techniques for detection of a resistance genomic DNA sequence include Southern hybridizations.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting a resistance protein, mRNA, or genomic DNA, such that the presence of the resistance protein, mRNA or genomic DNA is detected in the biological sample, and comparing the presence of the resistance protein, mRNA or genomic DNA in the control sample with the presence of the resistance protein, mRNA or genomic DNA in the test sample.

The invention also encompasses kits for detecting the presence of a resistance protein in a biological sample (a test sample). Such kits can be used to determine if a subject is suffering from or is at increased risk of developing a disorder associated with aberrant expression of a resistance (e.g., the presence of a drug resistant cancer). For example, the kit can comprise a labeled compound or agent capable of detecting a resistance protein or mRNA in a biological sample and means for determining the amount of the resistance protein in the sample (e.g., an antibody that binds to the resistance protein or an oligonucleotide probe which binds to DNA encoding a resistance protein, e.g., SEQ ID NO:1 or SEQ ID NO:2, SEQ ID NO:3, SEQ ID NO:5, SEQ ID NO:6, or a nucleic acid sequence depicted in Genbank Accession no.: X85993, L26081, L24118, M92357, M25324, M25280, W13166, X81627, K03235, U54705, or U04313). Kits may also include instruction for observing that the tested subject is suffering from or is at risk of developing a disorder associated with aberrant expression of the resistance sequence if the amount of resistance sequence is above or below a normal level.

For antibody-based kits, the kit may comprise, for example: (1) a first antibody (e.g., attached to a solid support) which binds to a resistance protein; and, optionally, (2) a second, different antibody which binds to the resistance protein or the first antibody and is conjugated to a detectable agent.

For oligonucleotide-based kits, the kit may comprise, for example: (1) a oligonucleotide, e.g., a detectably labeled oligonucleotide, which hybridizes to a resistance nucleic acid sequence or (2) a pair of primers useful for amplifying a selected resistance nucleic acid molecule;

The kit may also comprise, e.g., a buffering agent, a preservative, or a protein stabilizing agent. The kit may also comprise components necessary for detecting the detectable agent (e.g., an enzyme or a substrate). The kit may also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of the resistance sequence.

2. Prognostic Assays

The methods described herein can furthermore be utilized as diagnostic or prognostic assays to identify subjects having or at risk of developing a disease or disorder associated with aberrant resistance sequence expression or activity. For example, the assays described herein, such as the preceding diagnostic assays or the following assays, can be utilized to identify a subject having or at risk of developing a disorder associated with an aberrant resistance protein, nucleic acid expression, or activity (e.g., the presence of drug resistant tumor cells). Alternatively, the prognostic assays can be utilized to identify a subject having or at risk for developing such a disease or disorder. Thus, the present invention provides a method in which a test sample is obtained from a subject and a resistance sequence (e.g., mRNA, genomic DNA, or protein) is detected, wherein the presence or relative quantity of the resistance sequence is diagnostic for a subject having or at risk of developing a disease or disorder associated with aberrant expression or activity of the resistance sequence. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant expression or activity of a resistance nucleic acid or protein. Thus, if increased expression of an up-regulated resistance protein is a cause of increased drug resistance, such methods can be used to determine whether a subject can be effectively treated with a specific agent or class of agents (e.g., agents of a type which decrease the activity of the up-regulated protein). In the case of a down-regulated resistance sequence, e.g., maspin in an EMT6 tumor, detection of decreased expression of the down-regulated sequence can be used to determine whether a subject can be effectively treated with a specific agent or class of agents such as those that increase the activity of the down-regulated sequence. Thus, the present invention provides methods for determining whether a subject can be effectively treated with an agent for a disorder associated with aberrant resistance sequence expression or activity in which a test sample is obtained and the resistance sequence is detected (e.g., wherein the presence or relative quantity of the resistance sequence is diagnostic for a subject that can be administered the agent to treat a disorder associated with aberrant resistance sequence expression or activity). In some embodiments, the foregoing methods provide information useful in prognostication, staging and management of malignancies (tumors) that are characterized by altered expression of a resistance protein and thus by a drug-resistance phenotype. The information more specifically assists the clinician in designing chemotherapeutic or other treatment regimes to eradicate such malignancies from the body of an afflicted subject.

The methods of the invention can also be used to detect genetic lesions (e.g., mutations or amplifications) in a resistance gene, thereby determining if a subject with the altered gene is at risk for a disorder characterized by aberrant cell proliferation and/or differentiation. For example, genetic mutations, whether of germline or somatic origin, may indicate whether the process of developing drug resistance has been initiated or is likely to arise in the tested cells. In preferred embodiments, the methods include detecting, in a sample of cells from the subject, the presence or absence of a genetic lesion characterized by at least one of an alteration affecting the integrity of a gene encoding a resistance protein, the mis-expression of a resistance gene, or the amplification of a resistance gene. Preferably the sample of cells is obtained from a body tissue suspected of comprising transformed cells (e.g., cancer cells). Thus, the present method provides information relevant to diagnosis of the presence of a tumor.

Genetic lesions can be detected, for example, by ascertaining the existence of at least one of 1) a deletion of one or more nucleotides from a resistance gene; 2) an addition of one or more nucleotides to a resistance gene; 3) a substitution of one or more nucleotides of a resistance gene, 4) a chromosomal rearrangement of a resistance gene; 5) an alteration in the level of a messenger RNA transcript of a resistance gene, 6) aberrant modification of a resistance gene, such as of the methylation pattern of the genomic DNA; 7) the presence of a non-wild type splicing pattern of a messenger RNA transcript of a resistance gene, 8) a non-wild type level of a resistance-protein, 9) allelic loss of a resistance gene, 10) amplification of a resistance gene, and 11) inappropriate post-translational modification of a resistance-protein. As described herein, there are a large number of assay techniques known in the art which can be used for detecting lesions in a resistance gene. A preferred biological sample is a biopsy sample of tissue suspected of comprising transformed cells isolated by conventional means from a subject.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in a resistance gene (see Abravaya et al. (1995) *Nucleic Acids Res.* 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a resistance sequence (mRNA or DNA) under conditions such that hybridization and amplification of the resistance sequence (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self-sustained sequence replication (Guatelli et al. (1990) *Proc. Natl. Acad. Sci. USA* 87:1874–1878), transcriptional amplification system (Kwoh, et al. (1989) *Proc. Natl. Acad. Sci. USA* 86:1173–1177), Q-Beta Replicase (Lizardi et al. (1988) *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a resistance gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations in a resistance gene can be identified by hybridizing a sample and control nucleic acids, e.g., DNA or RNA, to high density arrays containing hundreds or thousands of oligonucleotides probes (Cronin et al. (1996) *Human Mutation* 7:244–255; Kozal et al. (1996) *Nature Medicine* 2:753–759). For example, genetic mutations in a resistance gene can be identified in two-dimensional arrays containing light-generated DNA probes as described in Cronin et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the resistance gene of interest and detect mutations by comparing the sequence of the sample resistance gene sequence with the corresponding wild-type (control) sequence. Additionally, sequencing of the DNA flanking a resistance gene can be used to determine if the resistance gene has been amplified. Examples of sequencing reactions include those based on techniques developed by Maxim and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Bio/Techniques* 19:448), including sequencing by mass spectrometry (see, e.g., PCT Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in a resistance gene include methods in which protection from cleavage agents is used to detect mismatched bases in RNA/RNA or RNA/DNA heteroduplexes (Myers et al. (1985) *Science* 230:1242). In general, the art technique of □mismatch cleavage□ starts by providing heteroduplexes of formed by hybridizing (labeled) RNA or DNA containing the wild-type resistance sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton et al (1988) *Proc. Natl Acad Sci USA* 85:4397; Saleeba et al (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called □DNA mismatch repair□ enzymes) in defined systems for detecting and mapping point mutations in cDNAs containing a resistance sequence obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a resistance sequence, e.g., a wild-type resistance sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in a resistance gene. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125–144; and Hayashi (1992) *Genet Anal Tech Appl* 9:73–79). Single-stranded DNA fragments of sample and control resistance nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition, it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a resistance sequence.

Furthermore, any cell type or tissue, preferably biopsy samples of tissue comprising or suspected of comprising transformed cells, in which a resistance sequence is expressed may be utilized in the prognostic assays described herein.

3. Pharmacogenomics

Agents, or modulators which have a stimulatory or inhibitory effect on expression or activity of a resistance sequence as identified by a screening assay described herein can be administered to individuals to treat (prophylactically or therapeutically) disorders (e.g., drug-resistance) associated with aberrant resistance sequence expression or activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of resistance protein, expression of resistance nucleic acid, or mutation content of a resistance gene in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) *Clin. Chem.* 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2Cl9) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C 19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of a resistance protein, expression of a resistance nucleic acid, or mutation content of a resistance gene in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a modulator of expression or activity of a resistance nucleic acid or protein, such as a modulator identified by one of the exemplary screening assays described herein.

4. Monitoring of Effects During Clinical Trials

Monitoring the influence of agents (e.g., drugs, compounds) on the expression or activity of a resistance nucleic acid or protein (e.g., the ability to modulate the drug-resistant phenotype of a cell) can be applied not only in basic drug screening, but also in clinical trials. For example, the effectiveness of an agent determined by a screening assay as described herein to decrease up-regulated resistance sequence expression or activity, decrease up-regulated resistance sequence expression or activity, increase down-regulated resistance sequence expression or activity, or expression or activity of a down-regulated resistance sequence can be monitored in clinical trials of subjects exhibiting increased or decreased resistance sequence expression or activity.

Alternatively, the effectiveness of an agent determined by a screening assay to increase up-regulated resistance sequence expression or activity (e.g., an agent that increases the drug resistance of a non-cancerous cell), can be monitored in clinical trials of compounds designed to increase up-regulated resistance sequence expression or activity. In such clinical trials, the expression or activity of an up-regulated resistance sequence and, optionally, other sequences that have been implicated in, for example, a cellular proliferation disorder, can be used as a "read out" or markers of the drug resistance of a particular cell. The effectiveness of a an agent determined to decrease the expression of a down-regulated resistance sequence can be monitored in a similar fashion. In this case, a decrease in down-regulated resistance sequence expression or activity is indicative of increased drug resistance.

For example, and not by way of limitation, genes, including a resistance gene, that are modulated in cells by treatment with an agent (e.g., compound, drug or small molecule) which modulates activity of a resistance sequence (e.g., identified in a screening assay as described herein) can be identified. Thus, to study the effect of agents on cellular proliferation disorders, for example, in a clinical trial, cells can be isolated and RNA prepared and analyzed for the levels of expression of a resistance sequence and other sequences (nucleic acid or polypeptide) implicated in the disorder. The levels of expression (i.e., a gene expression pattern) can be quantified by Northern blot analysis or RT-PCR, as described herein, or alternatively by measuring the amount of protein produced, by one of the methods as described herein, or by measuring the levels of activity of a resistance sequence or other sequence including a genes encoding such sequences. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a resistance sequence (e.g., protein, mRNA, or genomic DNA) in the preadministration sample; (iii) obtaining one or more post-administration samples from the subject; (iv) detecting the level of expression or activity of the resistance sequence in the post-administration samples; (v) comparing the level of expression or activity of the resistance sequence in the pre-administration sample with the resistance sequence in the post administration sample or samples; and (vi) altering the administration of the agent to the subject accordingly. For example, increased administration of the agent may be desirable to decrease the expression or activity of an up-regulated resistance sequence beyond what was detected in the post administration sample, i.e., to increase the effectiveness of the agent.

C. Methods of Treatment

The present invention provides for both prophylactic and therapeutic methods of treating a subject at risk of (or susceptible to) a disorder or having a disorder associated with aberrant resistance nucleic acid or protein expression or activity. Such disorders include cellular resistance to chemotherapeutic drugs.

1. Prophylactic Methods

In one aspect, the invention provides a method for preventing in a subject, a disease or condition associated with an aberrant resistance expression or activity (e.g., the development of drug resistance), by administering to the subject an agent which modulates expression of a resistance sequence (e.g., mRNA expression or protein expression) or at least one activity. Subjects at risk for a condition which is caused or contributed to by aberrant resistance nucleic acid or protein expression or activity can be identified by, for example, any or a combination of diagnostic or prognostic assays as described herein. Administration of a prophylactic agent can occur prior to the manifestation of symptoms characteristic of the resistance aberrancy, such that a disease or disorder is prevented or, alternatively, delayed in its progression. For example, administration of a prophylactic agent to a cancer patient may prevent or delay the development of drug resistance in the patient's cancer cells. Depending on the type of resistance aberrancy, for example, a resistance protein agonist or resistance protein antagonist agent can be used for treating the subject. The appropriate agent can be determined based on screening assays described herein.

2. Therapeutic Methods

Another aspect of the invention pertains to methods of modulating resistance nucleic acid or protein expression or activity for therapeutic purposes. For example, the effectiveness of chemotherapy is "potentiated" (enhanced) by restoring or improving vulnerability of the transformed cells to the cytotoxic effects of a chemotherapeutic drug that otherwise would be less effective by reducing the expression of a resistance sequence in the cells. The modulatory method of the invention involves contacting a cell with an agent that modulates one or more of the activities of resistance protein activity associated with the cell. An agent that modulates a resistance protein activity can be an agent as described herein, such as a nucleic acid or a protein, a naturally-occurring cognate ligand of a resistance protein, a peptide, a resistance peptidomimetic, or other small molecule. In one embodiment, the agent stimulates one or more of the biological activities of a resistance protein. Examples of such stimulatory agents include active resistance protein and a nucleic acid molecule encoding a resistance protein that has been introduced into the cell. Such agents are particularly useful for increasing expression or activity of a down-regulated resistance nucleic acid or protein in a drug resistant cell. In another embodiment, the agent inhibits one or more of the biological activities of a resistance protein. Examples of such inhibitory agents include antisense resistance nucleic acid molecules and anti-resistance protein antibodies. These modulatory methods can be performed in vitro (e.g., by culturing the cell with the agent) or, alternatively, in vivo (e.g, by administering the agent to a subject). Such methods are particularly useful for decreasing expression or activity of an up-regulated resistance nucleic acid or protein in a drug resistant cell. As such, the present invention provides methods of treating an individual afflicted with a disease or disorder characterized by aberrant expression or activity of a resistance sequence molecule. In one embodiment, the method involves administering an agent (e.g., an agent identified by a screening assay described herein), or combination of agents that modulates (e.g., up-regulates or down-regulates) resistance expression or activity. In another embodiment, the method involves administering a resistance sequence molecule (e.g., a nucleic acid or a protein) as therapy to compensate for reduced or aberrant resistance expression or activity.

For example, in one embodiment, the method involves administering the desired drug (e.g., cyclophosphamide) to an individual afflicted with a drug-resistant cell population (a tumor, e.g., a carcinoma, sarcoma, leukemia, lymphoma, or lymphosarcoma), and coadministering an inhibitor of an up-regulated resistance expression or activity; or administering an agent that increases the expression or activity of a down-regulated resistance nucleic acid or protein (e.g., maspin). The administration and coadministration steps can be carried out concurrently or in any order, and can be separated by a time interval sufficient to allow uptake of either compound by the cells to be eradicated. For example, an antisense pharmaceutical composition (or a cocktail composition comprising an antisense oligonucleotide targeted to an up-regulated resistance sequence in combination with one or more other antisense oligonucleotides) can be administered to the individual sufficiently in advance of administration of the chemotherapeutic drug to allow the antisense composition to permeate the individual's tissues, especially tissue comprising the transformed cells to be eradicated; to be internalized by transformed cells; and to disrupt resistance (e.g., up-regulated) sequence expression (e.g., disruption of expression of a resistance mRNA and/or resistance protein production).

In the case where it is desirable to increase the expression or activity of a resistance sequence (e.g., of a down-regulated resistance sequence) an additional sequences encoding the down-regulated sequence may be introduced or the regulatory sequences of the endogenous sequence altered using methods known in the art.

Inhibition of resistance activity is desirable in situations in which a resistance gene is abnormally up-regulated and/or in which decreased activity of a resistance sequence is likely to have a beneficial effect. Conversely, stimulation of a resistance protein activity is desirable in situations in which a resistance sequence is abnormally down-regulated and/or in which increased resistance sequence expression or activity is likely to have a beneficial effect.

This invention is further illustrated by the following examples which should not be construed as limiting. The contents of all references, patents and published patent applications cited throughout this application are hereby incorporated by reference.

EXAMPLES

Example 1

Isolation and Characterization of Resistance cDNA Sequences

In order to identify genes involved in drug resistance (i.e., resistance genes), mRNA expression in drug resistant EMT-6 tumors was compared to expression in non-drug resistant EMT-6 tumors. Drug resistant tumors were generated by injecting EMT-6 tumor cells (approximately $2 \times 10^6$ cells) subcutaneously into a mouse. When a tumor had developed whose volume was about 100 mm$^3$ (about 10 days post injection of cells), cisplatin or cyclophosphamide was injected (ip). Cisplatin was administered at a dosage of 10–30 mg/kg; cyclophosphamide was administered at a dosage of 150–300 mg/kg. Twenty-four hours after injection, the mouse was sacrificed, the tumor harvested, minced, and the resulting cell suspension was plated. The number of surviving cells in the suspension was determined using a Trypan Blue exclusion assay. The cycle of injection, drug treatment and tumor removal was repeated a total of 10–12 times to generate drug resistant tumors. Control tumors were generated using the same process except that saline was injected instead of a drug. To generate drug-resistant cell lines, the plated cells were passaged in culture rather than injected into mice.

The initial screening for differential expression of mRNA was performed using drug resistant EMT-6 tumors which were resistant to CDDP and control tumor. An Affimetryx GeneChip® (Affymetrix, Inc.) was used to analyze differential mRNA expression. Some of the sequences identified as having altered expression in a drug-resistant EMT-6 tumor as compared to a non-drug resistant EMT-6 tumor were further examined using Northern analysis. Northern analysis confirmed the differential expression of certain sequences identified in the initial screen. In this Northern analysis, RNA expression in three parent (non-drug resistant) EMT6 tumors and three CDDP (drug-resistant) EMT6 cell lines was compared. Sequences that were differentially expressed in these cells lines were selected for further study.

The expression analysis led to the identification of two types of sequences: (1) those whose expression was increased in drug resistant EMT6 tumors compared to non-drug resistant EMT6 tumors, and (2) those whose expression was decreased in drug-resistant EMT6 tumors compared to non-drug resistant EMT6 tumors.

Sequences selected from the initial screen whose differential expression was confirmed by Northern blot analysis were sequenced and then analyzed using the BLAST program. The identified cDNAs whose expression was increased in the drug resistant EMT6 tumors included those encoding semaphorin D (Genbank Accession No.: X85993; SEQ ID NO:1, FIGS. 1A–1B), B94 (Genbank Accession No.: L24118), mel-14 antigen (Genbank Accession No.: M25324; SEQ ID NO:2, FIGS. 2A–2B), 24p3 (Genbank Accession No.: X81627; SEQ ID NO:3; FIGS. 3A–3B) and proliferin (Genbank Accession No.: K03235). The cDNAs whose expression was decreased in the drug resistant EMT6 tumor included maspin (Genbank Accession No.: U54705; SEQ ID NO:5, FIG. 4; SEQ ID NO:6, FIG. 5).

In situ hybridization was used to further analyze expression of resistance expression. These studies confirmed the expression patterns of the identified genes in EMT-6 drug resistant tumors compared to EMT-6 non-drug resistant tumors.

Example 2

Expression of Resistance Sequences in Passaged EMT-6 Cell Lines and Other Cell Types Expression of the identified resistance sequences in EMT-6 cell lines that were passaged and in other tumor cell lines was examined using Northern analysis. These data are summarized in FIG. 6. It was found that expression of semaphorin D, B94, mel-14, 24p3, and proliferin remained elevated for a limited number of passages in drug resistant EMT-6 cell lines in the presence of CDDP. Similarly, expression of maspin in CDDP resistant EMT-6 cell lines was decreased for a limited number of passages. Expression of resistance sequences was examined in other cell lines. In general, not all drug resistant cell lines expressed altered levels of the identified resistance sequences. For example, semaphorin D was highly expressed in CDDP resistant SCC25 cells (a squamous cell carcinoma of the head and neck but not expressed or expressed at low levels in drug resistant A2780 cells (ovarian cancer cell line), UCLA cells (lung cancer cell line, U937 cells (leukemia cell line), or HL60 cells (leukemia cell line).

These data illustrate that resistance sequences may not be differentially expressed in all drug resistant cells or tumors. Such information is useful for applying the methods of the invention, e.g., for determining which sequences are preferred targets for therapeutic molecules in a given drug resistant tumor. For example, a sequence that is differentially expressed in cells derived from a particular type of drug resistant tumor would be a target for a therapeutic method in that tumor whereas a sequence that was not differentially regulated would be a less likely target.

Example 3

Preparation of Resistance Proteins

Recombinant resistance proteins can be produced in a variety of expression systems. For example, a mature resistance polypeptide can be expressed as a recombinant glutathione-S-transferase (GST) fusion protein in *E. coli* and the fusion protein can be isolated and characterized. Specifically, as described above, a resistance polypeptide can be fused to GST and this fusion protein can be expressed in *E. coli* strain PEB199. Expression of the GST-resistance fusion protein in PEB 199 can be induced with IPTG. The recombinant fusion protein can be purified from crude bacterial lysates of the induced PEB 199 strain by affinity chromatography on glutathione beads.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for determining whether a test compound is a candidate compound for modulating the drug resistance of an eukaryotic cell, the method comprising:
   a) determining the level of expression of a gene encoding a polypeptide comprising the amino acid sequence encoded by the nucleotide sequence of SEQ ID NO:1 in an eukaryotic cell in the presence of a test compound, wherein the gene is endogenous to the eukaryotic cell;
   b) determining the level of expression of the gene in the eukaryotic cell in the absence of the test compound; and
   c) identifying the test compound as a candidate modulator of drug resistance of the eukaryotic cell if the level of expression of the gene in the eukaryotic cell in the presence of the test compound differs from the level of expression of the gene in the eukaryotic cell in the absence of the test compound.

2. The method of claim 1, wherein the eukaryotic cell is a drug resistant cell.

3. The method of claim 1, wherein the drug resistant eukaryotic cell is a cancer cell.

4. The method of claim 1, wherein the candidate modulator increases expression of the gene.

5. The method of claim 1, wherein the candidate modulator decreases expression of the gene.

6. The method of claim 1, wherein the step of determining the level of expression comprises measuring mRNA expression.

7. The method of claim 1, wherein the step of determining the level of expression comprises measuring protein expression.

8. A method for determining whether a teat compound is a candidate compound for decreasing the drug resistance of an eukaryotic cell, the method comprising:
   a) determining the level of expression of a gene encoding a polypeptide comprising the amino acid sequence encoded by the nucleotide sequence of SEQ ID NO:1 in an eukaryotic cell in the presence of a test compound, wherein the gene is endogenous to the eukaryotic cell;
   b) determining the level of expression of the gene in the eukaryotic cell in the absence of the test compound; and
   c) identifying the test compound as a candidate compound for decreasing drug resistance of the eukaryotic cell if the level of expression of the gene in the eukaryotic cell in the presence of the test compound is less than the level of expression of the gene in the eukaryotic cell in the absence of the test compound.

9. A method for determining whether a test compound is a candidate compound for increasing the drug resistance of an eukaryotic cell, the method comprising:
   a) determining the level of expression of a gene encoding a polypeptide comprising the amino acid sequence encoded by the nucleotide sequence of SEQ ID NO:1 in an eukaryotic cell in the presence of a test compound, wherein the gene is endogenous to the eukaryotic cell;
   b) determining the level of expression of the gene in the eukaryotic cell in the absence of the test compound; and
   c) identifying the test compound as a candidate compound for increasing drug resistance of the eukaryotic cell if the level of expression of the gene in the eukaryotic cell in the presence of the test compound is more than the level of expression of the gene in the eukaryotic cell in the absence of the test compound.

10. The method of claim 8, wherein the eukaryotic cell is a drug resistant cell.

11. The method of claim 8, wherein the drug resistant eukaryotic cell is a cancer cell.

12. The method of claim 8, wherein the step of determining the level of expression comprises measuring mRNA expression.

13. The method of claim 8, wherein the step of determining the level of expression comprises measuring protein expression.

14. The method of claim 9, wherein the eukaryotic cell is a drug resistant cell.

15. The method of claim 9, wherein the drug resistant eukaryotic cell is a cancer cell.

16. The method of claim 9, wherein the step of determining the level of expression comprises measuring mRNA expression.

17. The method of claim 9, wherein the step of determining the level of expression comprises measuring protein expression.

18. The method of claim 12 wherein the step of measuring mRNA expression comprises a step of contacting mRNA present in the eukaryotic cell with a nucleic acid probe.

19. The method of claim 16 wherein the step of measuring mRNA expression comprises a step of contacting mRNA present in the eukaryotic cell with a nucleic acid probe.

20. The method of claim 18 wherein the nucleic acid probe is immobilized on a surface.

21. The method of claim 18 wherein the mRNA is immobilized on a surface.

22. The method of claim 12 wherein measuring mRNA expression comprises amplification of mRNA.

23. The method of claim 16 wherein measuring mRNA expression comprises amplification of mRNA.

24. The method of claim 18 or 19 wherein the nucleic acid probe is detectably labeled.

25. The method of claim 23 wherein the detectable label is selected from the group consisting of a fluorescent label, a radioactive label, and an enzymatic label.

26. The method of claim 18 or 19 wherein the probe comprises at least 15 contiguous nucleotides of the complement of the nucleotide sequence of SEQ ID NO:1.

27. The method of claim 18 or 19 wherein the probe comprises at least 30 contiguous nucleotides of the complement of the nucleotide sequence of SEQ ID NO:1.

28. The method of claim 18 or 19 wherein the probe comprises at least 50 contiguous nucleotides of the complement of the nucleotide sequence of SEQ ID NO:1.

29. The method of claim 18 or 19 wherein the probe comprises at least 100 contiguous nucleotides of the complement of the nucleotide sequence of SEQ ID NO:1.

30. The method of claim 13 wherein the step of measuring protein expression comprises a step of contacting protein present in the eukaryotic cell with an antibody.

31. The method of claim 17 wherein the step of measuring protein expression comprises a step of contacting protein present in the eukaryotic cell with an antibody.

32. The method of claim 29 or 30 wherein the antibody is detectably labeled.

33. The method of claim 31 wherein the detectable label is selected from the group consisting of a fluorescent label, a radioactive label, and an enzymatic label.

* * * * *

UNITED STATES PATENT AND TRADEMARK OFFICE
CERTIFICATE OF CORRECTION

PATENT NO. : 6,933,105 B2
DATED : August 23, 2005
INVENTOR(S) : Shengfang Jin

It is certified that error appears in the above-identified patent and that said Letters Patent is hereby corrected as shown below:

<u>Column 59,</u>
Line 54, delete "teat" and insert -- test --.

Signed and Sealed this

Twenty-eighth Day of March, 2006

JON W. DUDAS
*Director of the United States Patent and Trademark Office*